US012599577B2

(12) United States Patent
Fedorchak et al.

(10) Patent No.: US 12,599,577 B2
(45) Date of Patent: Apr. 14, 2026

(54) THERMORESPONSIVE GEL EYE DROP FOR OCULAR DELIVERY OF CYSTEAMINE

(71) Applicant: University of Pittsburgh—Of the Commonwealth System of Higher Education, Pittsburgh, PA (US)

(72) Inventors: Morgan Virginia Fedorchak, Mars, PA (US); Steven R. Little, Allison Park, PA (US); Joel S. Schuman, New York, NY (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 616 days.

(21) Appl. No.: 17/281,647

(22) PCT Filed: Nov. 18, 2019

(86) PCT No.: PCT/US2019/062028
§ 371 (c)(1),
(2) Date: Mar. 31, 2021

(87) PCT Pub. No.: WO2020/102810
PCT Pub. Date: May 22, 2020

(65) Prior Publication Data
US 2021/0369649 A1     Dec. 2, 2021

Related U.S. Application Data

(60) Provisional application No. 62/768,295, filed on Nov. 16, 2018.

(51) Int. Cl.
| | |
|---|---|
| *A61K 31/145* | (2006.01) |
| *A61K 9/00* | (2006.01) |
| *A61K 9/06* | (2006.01) |
| *A61K 9/16* | (2006.01) |
| *A61K 41/00* | (2020.01) |
| *A61K 47/32* | (2006.01) |
| *A61P 27/02* | (2006.01) |

(52) U.S. Cl.
CPC .......... *A61K 31/145* (2013.01); *A61K 9/0048* (2013.01); *A61K 9/06* (2013.01); *A61K 9/1647* (2013.01); *A61K 9/1694* (2013.01); *A61K 41/0028* (2013.01); *A61K 47/32* (2013.01); *A61P 27/02* (2018.01)

(58) Field of Classification Search
None
See application file for complete search history.

(56) References Cited

U.S. PATENT DOCUMENTS

| | | | |
|---|---|---|---|
| 5,837,226 A | 11/1998 | Jungherr et al. |
| 6,264,971 B1 | 7/2001 | Darougar et al. |
| 6,656,460 B2 | 12/2003 | Benita et al. |
| 7,060,299 B2 | 6/2006 | Alavattam et al. |
| 7,589,057 B2 | 9/2009 | Chang et al. |
| 8,298,569 B2 | 10/2012 | Philips et al. |
| 8,492,334 B2 | 7/2013 | Lavik et al. |
| 8,980,248 B2 | 3/2015 | Shoichet et al. |
| 9,018,006 B2 | 4/2015 | Stepkowski et al. |
| 9,056,045 B2 | 6/2015 | Hughes et al. |
| 9,655,862 B2 | 5/2017 | Mousa |
| 9,757,276 B2 | 9/2017 | Penhasi |
| 9,937,256 B2 | 4/2018 | Knipe et al. |
| 9,937,278 B2 | 4/2018 | Steinberg et al. |
| 10,376,592 B2 | 8/2019 | Acharya et al. |
| 10,624,865 B2 | 4/2020 | Pathak |
| 10,980,882 B2 | 4/2021 | Kang-Mieler et al. |
| 11,246,838 B2 | 2/2022 | Fedorchak et al. |
| 11,266,608 B2 | 3/2022 | Kang-Mieler et al. |
| 2001/0049369 A1 | 12/2001 | Jablonski et al. |
| 2002/0197300 A1 | 12/2002 | Schultz et al. |
| 2006/0018911 A1 | 1/2006 | Ault-Riche et al. |
| 2006/0173060 A1 | 8/2006 | Chang et al. |
| 2006/0235084 A1 | 10/2006 | Heller et al. |
| 2006/0246145 A1 | 11/2006 | Chang et al. |
| 2009/0252781 A1 | 10/2009 | Sawhney et al. |
| 2010/0209478 A1 | 8/2010 | Sawhney et al. |
| 2010/0261646 A1 | 10/2010 | Lavik et al. |
| 2011/0189291 A1 | 8/2011 | Yang et al. |

(Continued)

FOREIGN PATENT DOCUMENTS

| | | |
|---|---|---|
| WO | WO 2011/106702 | 9/2011 |
| WO | WO 2012/044952 | 4/2012 |

(Continued)

OTHER PUBLICATIONS

Luaces-Rodriguez, A., et al., Cysteamine polysaccharide hydrogels: Study of extended ocular delivery and biopermanence time by PET imaging, Jun. 19, 2017, Int. J. Pharmaceutics, vol. 528, 714-722. (Year: 2017).*

Wan, F., et al., Modulating protein release profiles by incorporating hyaluronic acid into PLGA microparticles via a spray dryer equipped with a 3-fluid nozzle, May 28, 2014, Pharm. Res., vol. 31, 2940-2951. (Year: 2014).*

Shams et al., "Treatment of corneal cystine crystal accumulation in patients with cystinosis," Clin. Ophthalmol, Oct. 2014, 8:2077-2084.

Aburahma et al., "Biodegradable ocular inserts for sustained delivery of brimonidine tartarate: preparation and in vitro/in vivo evaluation," AAPS PharmSciTech, Dec. 2011, 12(4):1335-1347.

(Continued)

*Primary Examiner* — Bethany P Barham
*Assistant Examiner* — Paul Hoerner
(74) *Attorney, Agent, or Firm* — Fish & Richardson P.C.

(57)          ABSTRACT

This document provided ocular delivery systems for treatment of cystinosis as well as methods for making such ocular delivery systems and methods for using such ocular delivery systems. For example, ocular delivery systems designed to include spray-dried, cysteamine-loaded microparticles suspended in a thermoresponsive gel are provided herein.

8 Claims, 20 Drawing Sheets

(56) References Cited

U.S. PATENT DOCUMENTS

| | | | |
|---|---|---|---|
| 2011/0206773 A1 | 8/2011 | Lavik et al. | |
| 2012/0040397 A1 | 2/2012 | Luo et al. | |
| 2012/0148676 A1 | 6/2012 | Little | |
| 2012/0156176 A1 | 6/2012 | Fujimoto et al. | |
| 2012/0231072 A1 | 9/2012 | Kang-Mieler et al. | |
| 2013/0189230 A1 | 7/2013 | Shoichet et al. | |
| 2014/0086975 A1 | 3/2014 | Sinko et al. | |
| 2014/0086995 A1 | 3/2014 | Ratner et al. | |
| 2014/0271863 A1 | 9/2014 | Anderson et al. | |
| 2014/0343413 A1 | 11/2014 | Jolek et al. | |
| 2014/0343476 A1 | 11/2014 | Penhasi | |
| 2015/0037422 A1 | 2/2015 | Kaplan et al. | |
| 2015/0087671 A1 | 3/2015 | McClain et al. | |
| 2015/0140106 A1 | 5/2015 | Mousa | |
| 2015/0374633 A1* | 12/2015 | Fedorchak | A61K 9/5021 514/249 |
| 2016/0058698 A1 | 3/2016 | Mayadunne et al. | |
| 2016/0166504 A1 | 6/2016 | Jarrett et al. | |
| 2016/0206741 A1 | 7/2016 | Knipe et al. | |
| 2017/0087248 A1 | 3/2017 | Kang-Mieler et al. | |
| 2017/0189546 A1 | 7/2017 | Bidwell, III et al. | |
| 2017/0348254 A1* | 12/2017 | O'Neil | A61K 9/0075 |
| 2019/0046479 A1 | 2/2019 | Pathak | |
| 2019/0099365 A1 | 4/2019 | Fedorchak et al. | |
| 2020/0246179 A1 | 8/2020 | Peyman | |
| 2020/0360282 A1 | 11/2020 | Fedorchak et al. | |
| 2020/0383928 A1 | 12/2020 | Kang-Mieler et al. | |
| 2022/0202705 A1 | 6/2022 | Fedorchak et al. | |
| 2022/0211632 A1 | 7/2022 | Fedorchak et al. | |

FOREIGN PATENT DOCUMENTS

| | | |
|---|---|---|
| WO | WO 2012/169972 | 12/2012 |
| WO | WO 2014/074823 | 5/2014 |
| WO | WO 2014/138085 | 9/2014 |
| WO | WO 2015/001087 | 1/2015 |
| WO | WO 2017/165449 | 9/2017 |
| WO | WO 2018/206749 | 11/2018 |

OTHER PUBLICATIONS

Babiuch, retrieved from the retinal physician website: www.retinalphysician.com/issues/2017/june-2017/ new-monoclonal-antibody-treatments-in-retina on Aug. 19, 2019, 4 pages.

Bald et al., "2-Chloro-1-Methylquinolinium Tetrafluoroborate as an Effective and Thiol Specific UV-Tagging Reagent for Liquid Chromatography," J. Liq. Chromatogr. Relat. Technologies, 2001, 24(9):1323-1339.

Berge et al., "Pharmaceutical salts," J. Pharm. Sci., 66(1):1-19, Jan. 1977.

Chang et al., "Biodegradable PLGA-based Drug Delivery Systems for Modulating Ocular Surface Disease under Experimental Murine Dry Eye," J. Clin. Exp. Ophthalmol., 2(11): 13 pages, Nov. 1, 2011.

Chen et al., "Selection and analysis of an optimized anti-VEGF antibody: crystal structure of an affinity-matured Fab in complex with antigen," J. Mol. Bio., 293(4):865-81, Nov. 1999.

Cui et al., "New Hydrolysis-Dependent Thermosensitive Polymer for an Injectable Degradable System," Biomacromolecules, 8(4):1280-1286, Apr. 2007.

Derwent and Mieler, "Thermoresponsive hydrogels as a new ocular drug delivery platform to the posterior segment of the eye," Transactions of the American Ophthalmological Society, 106:206-214, Dec. 2008.

Doiron et al., "Preparation and initial characterization of biodegradable particles containing gadolinium-DTPA contrast agent for enhanced MRI," Proc. Nat. Acad. Sci. USA, Nov. 11, 2008, 105(45):17232-17237.

Fedorchak et al., "28-day intraocular pressure reduction with a single dose of brimonidine tartrate-loaded microspheres," Experimental Eye Research, vol. 125, 210-216, Jun. 28, 2014.

Fedorchak et al., "28-Day Ocular Delivery of Brimonidine Tartrate from Rationally Designed Degradable Microparticles in a Rabbit Model," presentation delivered at AIChE annual meeting Oct. 31, 2012.

Fedorchak et al., "28-Day Ocular Delivery of Brimonidine Tartrate from Rationally Designed Degradable Microparticles in a Rabbit Model," presentation delivered at Society for Biomaterials Oct. 4, 2012.

Fedorchak et al., "Advanced Controlled Release Systems for Next Generation Ophthalmic Therapy," presentation delivered at Gordon Research Conference Mar. 22, 2012.

Fedorchak et al., "Combating Blindness with Convenient and Comfortable Glaucoma Treatments," presentation delivered at ARVO annual meeting May 4, 2012.

Fedorchak et al., "Combating Blindness with Convenient and Comfortable Glaucoma Treatments," presentation delivered at McGowan Institute for Regenerative Medicine annual retreat Mar. 5, 2012.

Friedman et al., "Prevalence of open-angle glaucoma among adults in the United States," Arch. Ophthalmol., Apr. 2004, 122(4):532-538.

Fujimoto et al., "Synthesis, Characterization and Therapeutic Efficacy of a Biodegradable, Thermoresponsive Hydrogel Designed for Application in Chronic Infarcted Myocardium," Biomaterials, 30(26):4357-4368, Sep. 2009.

Gao et al., "A Microparticle/Hydrogel Combination Drug-Delivery System for Sustained Release of Retinoids," Investigative Ophthalmology & Visual Science, 53:10, 6314-6323, Sep. 2012.

Ghate et al., "Barriers to Glaucoma Drug Delivery," J. Glaucoma, Mar. 2008, 17(2):147-156.

Gu et al., "Controlled release of recombinant human nerve growth factor (rhNGF) from poly [(lactic acid)-co-(glycolic acid)]microspheres for the treatment of neurodegenerative disorders," Polymer International, 56( 10): 1272-1280, Oct. 2007.

Guan et al., "Protein-reactive, Thermoresponsive Copolymers With High Flexibility and Biodegradability," Biomacromolecules, 9(4):1283-92, Apr. 2008.

Hermann et al., "Electronic compliance monitoring of topical treatment after ophthalmic surgery," Int. Ophthalmol., Apr. 7, 2010, 30:385-390.

Hu et al., "Controlled Release Bevacizumab in Thermoresponsive Hydrogel Found to Inhibit Angiogenesis," Biomed. Mater. Eng., 24:1941-50, 2014.

Ibrahim et al., "Novel Topical Ophthalmic Formulations for Management of Glaucoma," Pharmaceutical Research, 30(11): 2818-2831, Nov. 15, 2013.

Jimenez et al., "A sustained release cysteamine microsphere/thermoresponsive gel eyedrop for corneal cystinosis improves drug stability," Drug Deliv. Transl. Research, Feb. 4, 2021, 11(5):2224-2238.

Karamanos et al., "Development of an HPLC method for determining the alpha2-adrenergio receptor agonist brimonidine in blood serum and aqueous humor of the eye," Biomed. Chromatogr., 1999, 13:86-88.

Knight et al., "Sustained drug delivery in glaucoma," Current Opinion in Ophthamology, 25(2): 112-117, Mar. 2014.

Kusmierek et al., "Measurement of reduced and total mercaptamine in urine using liquid chromatography with ultraviolet detection," Biomed. Chromatography, Jan. 18, 2008, 22(4):441-445.

Lambiase et al., "Experimental and clinical evidence of neuroprotection by nerve growth factor eye drops: Implications for glaucoma," PNAS, 106(32): 13469-13474, Aug. 11, 2009.

Lee and Vernon, "In Situ-Gelling, Erodible N-isopropylacrylamide Copolymers," Macromol. Biosci., 5(7):629-635, Jul. 2005.

MacCallum et al., "Antibody-antigen Interactions: Contact Analysis and Binding Site Topography," J. Mol. Biai., 262(5):732-45, Oct. 1996.

Na et al., Langmuir 2010; 26:11165-11169.

Nanjawade et al., "In situ-forming hydrogels for sustained ophthalmic drug delivery," J. Control Release., 122(2):119-34, Sep. 2007.

Nussenblatt et al. Retina, 2013; 30:1579-1587. doi:10.1097/IAE.0b013e3181e7878e.

(56)          References Cited

OTHER PUBLICATIONS

Pascual-Camps et al. J. Ophthal. Inflann. Infect. 2014; 4:26. www.joii-journal.conn/content/4/1/26.

PCT International Preliminary Report on Patentability in International Appln. No. PCT/US2019/062028, dated May 18, 2021, 6 pages.

PCT International Search Report and Written Opinion in International Appln. No. PCT/US2019/062028, dated Mar. 19, 2020, 10 pages.

Pescina et al., "Effect of pH and penetration enhancers on cysteamine stability and trans-corneal transport," Eur. J. Pharm. Biopharmaceutics, Oct. 2016, 107: 171-179.

Rudikoff et al., "Single amino acid substitution altering antigen-binding specificity." Proc. Natl. Acad. Sci. U.S.A., 79(6):1979-1983, Mar. 1982.

Sánchez et al., "Development of biodegradable microspheres and nanospheres for the controlled release of cyclosporin A," Int. J. Pharmaceutics, Oct. 15, 1993, 99(2-3):263-273.

Shanbhag et al., "Macrophage/particle interactions: effect of size, composition and surface area," J. Biomed. Mater. Res., Jan. 1994, 28(1):81-90.

Turturro et al., "The effects of cross-linked thermo-responsive PNIPAAm-based hydrogel injection on retinal function," Biomaterials, 32(14):3620-6, May 2011.

Wang et al., "Novel Thermosensitive Hydrogel Injection Inhibits Post-Infarct Ventricle Remodelling," Eur. J. Heart Fail, 11(1):14-19, Jan. 2009.

Wang et al., "Synthesis, Characterization and Surface Modification of Low Moduli Poly(ether Carbonate Urethane)ureas for Soft Tissue Engineering," Acta. Biomater., 5(8):2901-12, Oct. 2009.

Wang et al., "The nerve growth factor signaling and its potential as therapeutic target for glaucoma." BioMed Research International, Aug. 31, 2014.

Wikipedia.org [online], "Cysteamine," dated Sep. 7, 2018, retrieved from URL<https://en.wikipedia.org/w/index.php?title=Cysteamine&oldid=858431558>, 5 pages.

Wikipedia.org [online], "Freeze drying," dated Nov. 6, 2018, retrieved from URL<https://en.wikipedia.org/w/index.php?title=Freeze-drying&oldid=924871987>, 12 pages.

Wu et al., "Humanization of a murine monoclonal antibody by simultaneous optimization of framework and CDR residues," J. Mol. Biol., 294(1):151-162, Nov. 1999.

Wu et al., "Toward the development of partially biodegradable and injectable thermoresponsive hydrogels for potential biomedical applications," ACS Appl. Mater. Interf., 1(2):312-327, Feb. 2009.

Xu et al. Macromolecules, 2007; 40:9103-9110.

Yang et al., "Hybrid Dendrimer Hydrogel/PLGA Nanoparticle Platform Sustains Drug Delivery for One Week and Antiglaucoma Effects for Four Days Following One-Time Topical Administration," ACS Nano, 6(9): 7595-7606, Aug. 9, 2012.

Zhang and Zhuo, "Synthesis and in vitro drug release behavior of amphiphilic triblock copolymer nanoparticles based on poly (ethylene glycol) and polycaprolactone," Biomaterials, 26(33):6736-42, Nov. 2005.

Zhang et al., "Absolute quantification of poly(dl-lactide-co-glycolide) in microspheres using quantitative 1H NMR spectroscopy," J. Pharm. Biomed. Analysis, Nov. 30, 2017, 146:273-278.

Zweers et al., "Release of anti-restenosis drugs from poly(ethylene oxide)-poly(dl-lactic-co-glycolic acid) nanoparticles," J. Control. Release, Sep. 12, 2006, 114(3):317-324.

Bhagav et al., "Sustained release ocular inserts of brimonidine tartrate for better treatment in open-angle glaucoma," Drug Deliv. Transl. Res., Apr. 2011, 1(2):161-174.

Fedorchak et al., "Long Term Glaucoma Drug Delivery Using a Topically Retained Gel/Microsphere Eye Drop," Sci. Rep., Aug. 2017, 7:8639.

U.S. Appl. No. 17/577,816, filed Jan. 18, 2022, Morgan V. Fedorchak, Published as U.S. Publication No. 2022/0202705.

U.S. Appl. No. 17/580,988, filed Jan. 21, 2022, Morgan V. Fedorchak, Published as U.S. Publication No. 2022/0211632.

Maren et al., "Ocular pharmacology of methazolamide analogs: distribution in the eye and effects on pressure after topical application," J. Pharmacol. Exp. Ther., Apr. 1987, 241(1):56-63.

Park et al., "An anti-angiogenic reverse thermal gel as a drug-delivery system for age-related wet macular degeneration," Macromol. Biosci., Apr. 2013, 13(4):464-469.

U.S. Appl. No. 14/772,758, filed Sep. 3, 2015, Steven R. Little, Published as U.S. Patent Publication No. 2015/0374633.

U.S. Appl. No. 16/087,470, filed Sep. 21, 2018, Morgan Virginia Fedorchak, Published as U.S. Patent Publication No. 2019/0099365.

* cited by examiner

FIG. 1A
FIG. 1C
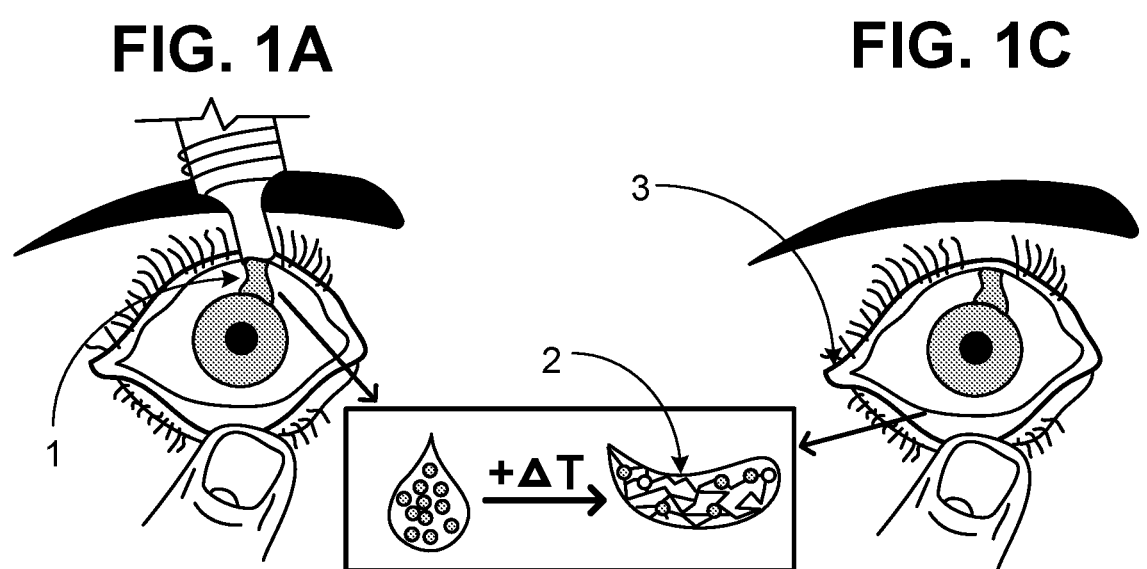
FIG. 1B
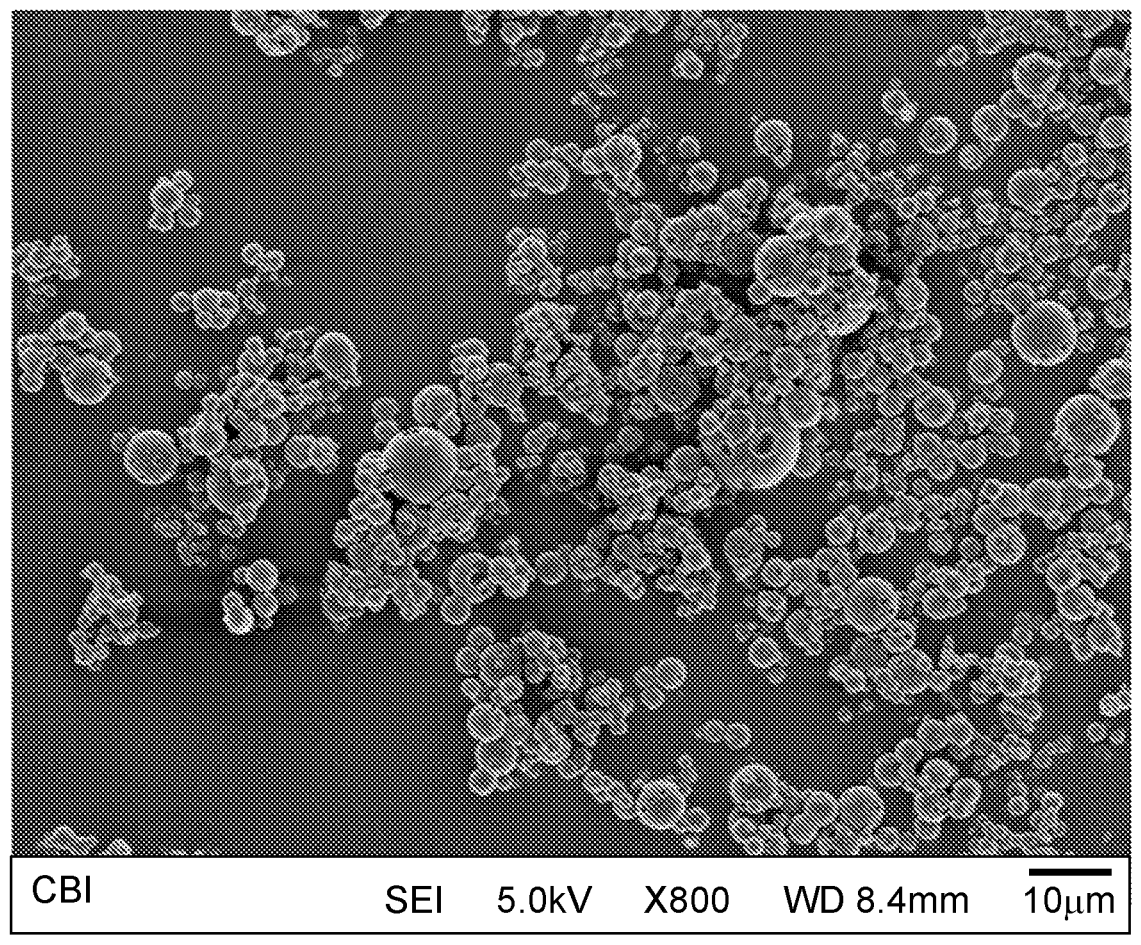
FIG. 2

| CBI | | SEI | 3.0kV | X3.000 | WD 7.5mm | 1μm |

CTNS -/-

Control

$$y = 1.6646x + 5.4822$$
$$R^2 = 0.97397$$

CBI        SEI        3.0kV        X3.000        WD 7.7mm        1μm

THERMORESPONSIVE GEL EYE DROP FOR OCULAR DELIVERY OF CYSTEAMINE

CROSS-REFERENCE TO RELATED APPLICATIONS

This application is a National Stage application under 35 U.S.C. § 371 of International Application No. PCT/US2019/062028, having an International Filing Date of Nov. 18, 2019, which claims priority to U.S. Patent Application Ser. No. 62/768,295, filed on Nov. 16, 2018. The disclosure of the prior applications are considered part of (and are incorporated by reference in) the disclosure of this application.

BACKGROUND

1. Technical Field

This document relates to ocular delivery systems comprising spray-dried, cysteamine-loaded microparticles suspended in a thermoresponsive gel. For example, this document provides such systems, methods of making such systems, and methods for using such systems.

2. Background Information

Cystinosis is a rare lysosomal storage disease in which cysteine accumulates in organs and tissues throughout the body. Corneal cystinosis is characterized by deposition of cystine crystals in the eyes. Currently, the only treatment for corneal cystinosis is cysteamine eye drops (Cystaran® eye drops, Sigma-Tau Pharmaceuticals, Inc., Gaithersburg, MD) that are administered once per waking hour to help dissolve the cystine crystals. The eye drops, which must be administered for a lifetime, are highly irritating and unstable, lasting only about one week in refrigeration. There is a need for more stable eye drops that can be administered less frequently, e.g., once per day or less.

SUMMARY

Embodiments of an ocular delivery system comprising spray-dried, cysteamine-loaded microparticles suspended in a thermoresponsive gel are disclosed. Methods of making and using the ocular delivery system are also disclosed.

Embodiments of the disclosed ocular delivery system for cysteamine comprise a thermoresponsive gel and a plurality of spray-dried microparticles comprising a biodegradable polymer and cysteamine or a pharmaceutically acceptable salt thereof. In some embodiments, the biodegradable polymer comprises polyglycolide (PGA), poly(lactic acid) (PLA), poly(lactic-co-glycolic acid) (PLGA), or any combination thereof. In certain embodiments, the biodegradable polymer comprises PLGA. In any or all embodiments, the thermoresponsive gel may comprise poly(N-isopropyl acrylamide) (PNIPAAm).

In any or all embodiments, the cysteamine or the pharmaceutically acceptable salt thereof may be homogeneously dispersed within the spray-dried microparticles. In any or all embodiments, the spray-dried particles may comprise from 10-20 wt % cysteamine or an amount of a pharmaceutically acceptable salt of cysteamine sufficient to provide 10-20 wt % cysteamine. In some embodiments, the ocular delivery system comprises from 0.001 mg to 0.5 mg of the spray-dried microparticles per microliter of the ocular delivery system. In any or all embodiments, the spray-dried microparticles may have a volume average diameter within a range of from 200 nm to 10 μm.

Embodiments of a process for making the disclosed ocular delivery systems for cysteamine include (i) providing a liquid feedstock comprising cysteamine or a pharmaceutically acceptable salt thereof, a biodegradable polymer, and a solvent; (ii) directing the liquid feedstock to a spray-drying apparatus comprising a drying chamber comprising an inlet and an outlet, a nozzle coupled to the inlet, a spray gas source coupled to the nozzle, a separator coupled to the outlet of the drying chamber, and an aspirator coupled to the separator; (iii) atomizing the liquid feedstock into droplets as the liquid feedstock flows through the nozzle and into the drying chamber; (iv) removing at least a portion of the solvent from the droplets in the drying chamber, thereby forming a plurality of spray-dried microparticles, wherein the spray-dried microparticles comprise a solid dispersion of the cysteamine, or the pharmaceutically acceptable salt thereof, and the biodegradable polymer; (v) collecting the spray-dried microparticles; and (vi) dispersing the spray-dried microparticles in a thermoresponsive gel to form an ocular delivery system for cysteamine. In some embodiments, the drying chamber has an inlet temperature within a range of 25 to 75° C. and an outlet temperature within a range of 30 to 55° C.

In any or all embodiments, (i) the liquid feedstock may comprise 0.1-10 wt % cysteamine or an amount of pharmaceutically acceptable salt of cysteamine sufficient to provide 0.1-10 wt % cysteamine; or (ii) the liquid feedstock may have a weight ratio of biodegradable polymer to cysteamine within a range of from 2 to 20; or (iii) the liquid feedstock may have a total solids content within a range of from 2-12 wt %; or (iv) any combination of (i), (ii), and (iii).

Embodiments of a method for treating cystinosis include administering a therapeutically effective amount of an ocular delivery system as disclosed herein at periodic intervals to each eye of a subject identified as having cystinosis, wherein the ocular delivery system forms a gelled member following administration to the eye. In some embodiments, administering the therapeutically effective amount comprises placing one to two drops of the ocular delivery system into a lower fornix of each eye, each drop having a volume of 25-75 μL. The periodic intervals may be from one to seven days. In any or all embodiments, the method may further include, after each of the periodic intervals, removing the gelled member prior administering a subsequent therapeutically effective amount of the ocular delivery system to each eye of the subject.

The foregoing and other objects, features, and advantages of the invention will become more apparent from the following detailed description, which proceeds with reference to the accompanying figures.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 1A-1C illustrate an exemplary method for administering an embodiment of a microparticle/thermoresponsive gel ocular delivery system as disclosed herein.

FIG. 2 is a scanning electron microscopy (SEM) photograph of cysteamine hydrochloride (HCl)/PLGA microparticles obtained with one embodiment of the disclosed process.

FIG. 13A is a cysteamine HCl calibration curve. FIG. 13B is a HPLC chromatogram showing detection of cysteamine-HCl (Cys-HCl) and 2-chloro-1-methylquinolinium tetrafluoroborate (CMQT).

FIG. 14A is an image of a DE-CMS. FIG. 14B is a graph showing cysteamine release over about 24 hours.

FIG. 15A is an image of SD-CMSs. FIG. 15B is a graph showing cysteamine release over about 8 hours.

FIG. 18A is a LC-MS spectra showing detection of cysteamine at an exact mass of 78.03997 and cystamine at an exact mass of 153.0513. FIG. 18B is a LC-MS spectra showing detection of CMQT at an exact mass of 178.04141. FIG. 18C is a LC-MS spectra showing detection of CMQT-cysteamine derivative at an exact mass of 219.09489.

FIG. 20A is a nuclear magnetic resonance (NMR) spectrum showing the detection of cysteamine. FIG. 20B is a graph showing the stability of cysteamine in SD-CMSs suspended in a thermoresponsive gel matrix as compared to a commercial eye drop.

DETAILED DESCRIPTION

Figure 3:
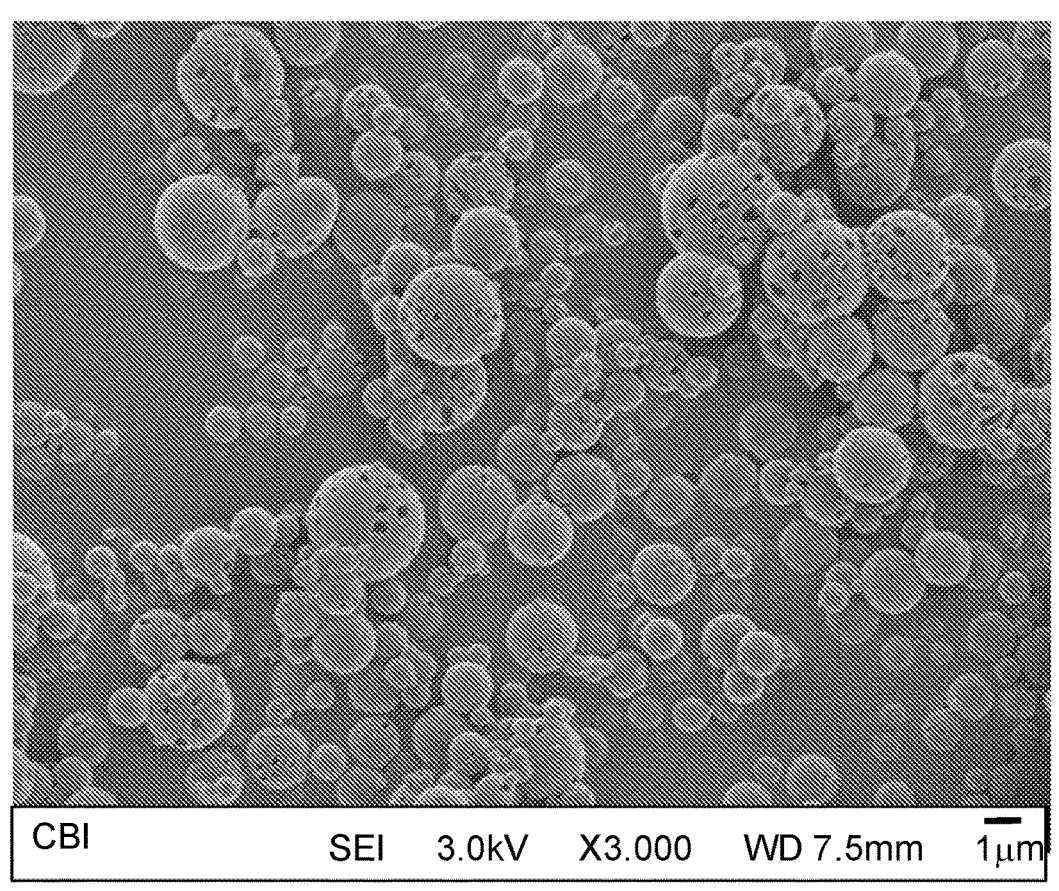
FIG. 3 is an SEM image of cysteamine hydrochloride/PLGA microparticles obtained with another embodiment of the disclosed process.

Disclosed herein are microparticle/thermoresponsive gel ocular delivery systems for cysteamine or a pharmaceutically acceptable salt thereof and methods of using the ocular delivery system. Processes for making the ocular delivery system are also disclosed.

Definitions and Abbreviations

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing embodiments from discussed prior art, the embodiment numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2).

In order to facilitate review of the various embodiments of the disclosure, the following explanations of specific terms are provided:

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats.

The term "biodegradable" means capable of being decomposed by a living organism, e.g., by a biological process.

"Cystamine" is a disulfide having the formula $H_2N(CH_2)_2S—S(CH_2)_2NH_2$. Cystamine is formed when cysteamine is oxidized.

"Cysteamine" is a cystine-depleting agent having the chemical formula $HS(CH_2)_2NH_3$ or a pharmaceutically acceptable salt thereof, e.g., $HS(CH_2)_2NH_2 \cdot HCl$.

A "feedstock" is a liquid composition (solution or suspension) that is spray dried.

A "gel" is a colloidal system comprising a solid three-dimensional network within a liquid. By weight, a gel may be primarily liquid, but behaves like a solid due to a three-dimensional network of entangled and/or crosslinked molecules of a solid within the liquid. From a rheological perspective, a gel has a storage modulus G' value which exceeds that of the loss modulus G". The storage modulus and loss modulus can be determined with a rheometer.

A "thermoresponsive gel" is a three-dimensional network of polymeric chains that are capable of absorbing and retaining molecules (e.g., water, polar solvents, non-polar solvents, drugs in liquid form, or the like) in their three-dimensional networks, wherein the gel undergoes a change from a hydrophilic state to a hydrophobic state as temperature changes. Thermoresponsive gel-forming polymeric chains may comprise one or more hydrophilic functional groups in their polymeric structures, such as amino ($NH_2$), hydroxyl (OH), amide (—CONH—, —$CONH_2$), sulfate (—$SO_3H$), or any combination thereof, and can be natural-, or synthetic-polymeric-based networks. In some embodiments, the polymeric chains can comprise a plurality of the same monomeric units. In other embodiments, the polymeric chains can comprise a plurality of different monomeric units.

"Inhibiting" refers to inhibiting the full development of a disease or condition. "Inhibiting" also refers to any quantitative or qualitative reduction in biological activity or binding, relative to a control. As used herein with respect to cystinosis, inhibiting refers to reducing an amount of cystine crystal formation or preventing cystine crystal formation in a subject's eyes relative to an amount of crystal formation in the absence of administering the disclosed ocular delivery system.

"Lower Critical Solution Temperature" (LCST) refers to a critical temperature at or above which a thermoresponsive gel can undergo a change from its hydrophilic state to its hydrophobic state, or vice versa. In some embodiments, a thermoresponsive gel is hydrated below its LCST, and therefore is hydrophilic. In some embodiments, a thermoresponsive gel is at least partially dehydrated above its LCST, and therefore is insoluble and hydrophobic. In some embodiments, LCST of linear thermo-responsive polymers is determined using cloud point (CP), and is generally used for physically crosslinked polymers. Cloud point refers to the temperature at the outset of cloudiness, the temperature at inflection point of a transmittance curve, or the temperature at a defined transmittance. The cloud point can be affected by many structural parameters of the thermoresponsive gel like the hydrophobic content, architecture of the thermoresponsive gel, molar mass of the thermoresponsive gel, or any combinations thereof.

"Microparticle," as used herein, unless otherwise specified, generally refers to a particle of a relatively small size, but not necessarily in the micron size range; the term is used in reference to particles of sizes that can be, for example, administered to the eye in the form of an eye drop that can be delivered from a squeeze nozzle container, and thus can be less than 50 nm to 100 microns or greater. In certain embodiments, microparticles specifically refers to particles having a diameter from 0.2 to 25 microns, such as from 0.2 to 10 microns. In one embodiment, the particles have a diameter from 0.2 to 10 microns, 0.2 to 5 microns, or 0.2 to 3 microns. As used herein, the microparticle encompasses microspheres, microcapsules, microparticles, microrods, nanorods, nanoparticles, or nanospheres unless specified otherwise. A microparticle may be of composite construction and is not necessarily a pure substance; it may be spherical or any other shape.

A "polymer" is a molecule of repeating structural units (e.g., monomers) formed via a chemical reaction, i.e., polymerization. A "copolymer" is a polymer formed from polymerization of two or more different monomers. Simultaneous polymerization of two or more different monomers generally produces a "random copolymer." Unless otherwise specified, polymer molecular weights provided herein are weight average molecular weight, Mw.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition. For example, a "therapeutically effective amount" may be a level or amount of agent needed to treat an ocular condition, or reduce or prevent ocular injury or damage without causing significant negative or adverse side effects to the eye or a region of the eye.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the course of a disease, for example, in a subject who has cystinosis. In certain embodiments, "treating" means reduction or resolution of cystinosis, e.g., as indicated by an amount of degree of cystine crystal formation in the eyes, particularly the corneas, of a subject having cystinosis. Cystine crystal formation may be reduced or completely inhibited relative to an amount of cystine crystal formation in the absence of treatment.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, PA (19th Edition).

The term "pharmaceutically acceptable salt" refers to salts prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. These salts may be prepared by standard procedures, for example by reacting the free acid with a suitable organic or inorganic base. Any chemical compound recited in this specification may alternatively be administered as a pharmaceutically acceptable salt thereof "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). Such salts are known to those of skill in the art. For additional examples of "pharmacologically acceptable salts," see Berge et al., *J. Pharm. Sci.* 66:1 (1977). The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethane-dioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

Cysteamine Ocular Delivery Systems and Methods of Use

Disclosed herein are microparticle/thermoresponsive gel ocular delivery systems for cysteamine or a pharmaceutically acceptable salt thereof. Hereinafter, unless specified otherwise, the term "cysteamine" is understood to refer to cysteamine free base or a pharmaceutically acceptable salt of cysteamine, e.g., cysteamine hydrochloride. The ocular delivery systems disclosed herein are noninvasive since a microparticle/thermoresponsive gel suspension can be self-administered to the lower fornix and removed by the subject (e.g., with tweezers or a saline solution).

The ocular delivery system comprises spray-dried microparticles dispersed in a thermoresponsive gel, the microparticles comprising cysteamine and a polymer. The polymers for the spray-dried microparticles may be biodegradable polymers so long as they are biocompatible (i.e., do not produce adverse effects (toxicity, irritation, etc.) when administered to a subject). Preferred biodegradable polymers are polyhydroxyacids such as polylactic acid and copolymers thereof. Illustrative polymers include polyglycolide (PGA), poly(lactic acid) (PLA), and poly(lactic-co-glycolic acid) (PLGA). Another class of approved biodegradable polymers is the polyhydroxyalkanoates. The percent loading of an agent, such as cysteamine, may be increased by "matching" the hydrophilicity or hydrophobicity of the polymer to the agent to be encapsulated. In some cases, such as PLGA, this can be achieved by selecting the monomer ratios so that the copolymer is more hydrophilic for hydrophilic drugs or less hydrophilic for hydrophobic drugs.

In some embodiments, the polymer is a PLGA copolymer. The weight average molecular weight of PLGA is from 4 kDa to 80 kDa, such as from 4 kDa to 50 kDa, or from 4 kDa to 15 kDa. The ratio of lactide to glycolide is from about 75:25 to about 50:50. In one embodiment, the ratio is 75:25. The molecular weight of the PLGA may control the degradation rate of the microparticles and subsequent drug release kinetics. Illustrative polymers include, but are not limited to, poly(D,L-lactic-co-glycolic acid) (PLGA, 75:25 lactic acid to glycolic acid ratio, $MW_w$=4-15 kDa, referred to as 752H); poly(D,L-lactic-co-glycolic acid) (PLGA, 50:50 lactic acid to glycolic acid ratio, $MW_w$=24-38 kDa, referred to as 503H); poly(D,L-lactic-co-glycolic acid) (PLGA, 50:50 lactic acid to glycolic acid ratio, $MW_w$=38-54 kDa, referred to as 504H); and poly(D,L-lactic-co-glycolic acid) (PLGA, 50:50 lactic acid to glycolic acid ratio, $MW_w$=38-54 kDa, referred to as 504). In certain examples, the polymer is PLGA 752H.

In some embodiments, the polymer is PLA. The weight average molecular weight may be from 20-80 kDa, such as from 20-50 kDa or 20-30 kDa.

In some embodiments, polymer chains in the thermoresponsive gel are not crosslinked. Absence of crosslinking removes barriers to diffusion. In certain embodiments, a wide range of molecular weights as described above and/or polymer concentrations are effective so long as the concentration provides a thermoresponsive gel that forms a gel below the lower critical solution temperature.

In some embodiments, the amount of cysteamine loaded into the spray-dried microparticles may be from 0.05 mg to 1 mg, such as 0.06-0.4 mg or 0.1-0.2 mg cysteamine free base (or an amount of a cysteamine salt sufficient to provide the desired amount of cysteamine free base) per milligram of microparticles. In certain embodiments, the amount of cysteamine loaded into the microparticles is 150-250 μg cysteamine per mg of microparticles. When the cysteamine is present as cysteamine hydrochloride, the amount loaded into the microparticles may be 0.1-1 mg, such as 0.1-0.5 mg or 0.15-0.25 mg cysteamine hydrochloride per mg of microparticles.

The cysteamine-loaded spray-dried microparticles may have a volume average diameter of 200 nm to 10 μm, such as 200 nm to 5 μm. In certain embodiments, the spray-dried microparticles do not have a volume average diameter of 10 μm or greater since such larger particles are difficult to eject from a container in the form of an eye drop.

The spray-dried microparticles are dispersed in a thermoresponsive gel. Advantageously, the selected thermoresponsive gel has a lower critical solution temperature (LCST) below body temperature. The thermoresponsive gel remains fluid below physiological temperature (e.g., 37° C. for humans) or at or below room temperature (e.g., 25° C.), solidifies (into a hydrogel) at physiological temperature, and is biocompatible. For example, the thermoresponsive gel may be a clear liquid at a temperature below 34° C. which reversibly solidifies into a gelled composition at a temperature above 34° C. Generally, the LCST-based phase transition occurs upon warming in situ as a result of entropically-driven dehydration of polymer components, leading to polymer collapse. Various naturally derived and synthetic polymers exhibiting this behavior may be utilized. Natural polymers include elastin-like peptides and polysaccharides derivatives, while notable synthetic polymers include those based on poly(N-isopropyl acrylamide) (PNIPAAm), poly (N,N'-dimethylacrylamide-co-N-phenylacrylamide), poly (glycidyl methacrylate-co-N-isopropylacrylamide), poly (ethylene oxide)-b-poly(propylene oxide)-b-poly(ethylene oxide), poly(ethylene glycol)-polyester copolymer, and amphiphilic block copolymers. In some embodiments, the thermoresponsive gel is PNIPAAm. The structure of PNIPAAm, containing both hydrophilic amide bonds and hydrophobic isopropyl groups, leads to a sharp phase transition at the LCST. Studies suggest that the average number of hydrating water molecules per NIPAAm group falls from 11 to about 2 upon the hydrophobic collapse above the LCST (32-34° C.).

In some embodiments, the thermoresponsive gel is non-biodegradable, e.g., PNIPAAm or a copolymer of N-isopropylacrylamide and at least one acrylic and/or methacrylic monomer. In certain embodiments, the $MW_w$ of the polymer or copolymer may be 5-20,000 kDa. In certain embodiments, the mol % for the N-isopropylacrylamide monomer in the copolymerization reaction may be 50-99 mol %. Illustrative acrylic monomers include an acrylate such as an alkyl acrylate (e.g., methyl acrylate, ethyl acrylate, butyl acrylate or 2-ethylhexyl acrylate), an acrylamide; or an acrylic acid or salt (e.g., 2-ethylacrylic acid, 2-propylacrylic acid, N-acryloxysuccinimide). Illustrative methacrylic monomers include a methacrylate (e.g., 2-hydroxymethacrylate, hydroxyethyl methacrylate, butyl methacrylate, methyl ether methacrylate or methyl methacrylate); a methacrylamide; or a methacrylic acid or salt. In certain embodiments, the acrylate monomer or methacrylate monomer may be modified with poly(ethylene glycol) to provide a co-poly (ethylene glycol) acrylate or co-poly(ethylene glycol) methacrylate prior to reaction with the N-isopropylacrylamide monomer. Acrylated PEG monomer(s) can be added in an amount of 1-15 mol %.

In other embodiments, the thermoresponsive gel is biodegradable. For example, biodegradable NIPAAm-based polymers can be made by conjugating the PNIPAAm with natural biodegradable segments such as MMP-susceptible peptide, gelatin, collagen, hyaluronic acid and dextran. Copolymers formed from NIPAAm and monomers with degradable side chains comprise another category of NIPAAm-based bioabsorbable, thermoresponsive gels.

Upon ocular administration of the ocular delivery system (i.e., the microparticle/thermoresponsive gel liquid suspension), the microparticle/thermoresponsive gel system releases water and can become an opaque solid gelled member. The gelled member may be sufficiently firm that it can be manipulated with tweezers. FIG. 1A depicts administration of an eye drop 1 comprising the microparticle/thermoresponsive gel liquid suspension, gelling of the suspension to form a polymeric crosslinked matrix 2 that encapsulates the cysteamine-loaded microparticles (FIG. 1B), and positioning of the resulting gelled member 3 in the lower fornix of the eye (FIG. 1C). In one particular embodiment, a thermoresponsive gel carrier for the cysteamine-loaded microparticles has been developed and characterized that will allow patients to apply a liquid suspension (containing the release system) topically to their eye as they would an aqueous eye drop-based medication (FIG. 1A). When the drop collects in the conjunctival cul-de-sac, the liquid warms to body temperature and the thermoresponsive gel de-swells, forming a stable, opaque gel (FIG. 1B). The drop also appears to naturally conform to the shape of the inferior fornix during the gelation (FIG. 1C) promoting retention of the system and continuous delivery of cysteamine to the eye via the embedded, sustained cysteamine microparticle formulation. The gel/microparticle ocular delivery system could afford sustained release of cysteamine for up to 30 times longer than any currently known in situ forming thermoresponsive gels. Furthermore, removal of the gelled drop would be as simple as flushing the eye with cold saline, unlike intravitreal or subconjunctival implants that require removal by a clinician.

The shape of the gelled member 3 may vary and is dependent on the anatomy of the ocular structure. Typically, the gelled member 3 spreads out into an elongate, thin film of gel, but it may assume a more cylindrical shape. In certain embodiments, the gelled film may have a thickness of 10 to 1000 more particularly 100 to 300 μm. The gel can be manipulated as it undergoes phase transitioning into a desired shape. In certain embodiments, the gelled member may retain pliability to a certain extent. In certain embodiments, the gelled member 3 may have a residence time in the lower fornix of at least one day, such as at least three days, at least five days, or at least seven days.

The ocular delivery system disclosed herein may provide for sustained release of cysteamine. For example, the sustained release may be over a period of at least one day, such as at least three days, at least five days, or at least seven days. The cysteamine release can be linear or non-linear (single or multiple burst release). In certain embodiments, the cysteamine may be released without a burst effect. For example, the sustained release may exhibit a substantially linear rate of release of the cysteamine in vivo over a period of at least one day, such as at least three days, at least five days, or at least seven day. By substantially linear rate of release it is meant that the cysteamine is released at a rate that does not vary by more than about 20% over the desired period of time, more usually by not more than about 10%. It may be desirable to provide a relatively constant rate of release of the cysteamine from the delivery system over the life of the system. For example, it may be desirable for the cysteamine to be released in amounts from 20 to 250 µg per day, more particularly 20 to 200 µg per day, for the life of the system. However, the release rate may be either increased or decreased depending on the formulation of the polymer microparticle and/or thermoresponsive gel. The desired release rate and target drug concentration can vary depending on the severity of the corneal cystinosis and the subject's overall health.

In certain embodiments, the cysteamine release is dependent on degradation of the polymer microparticles. As the polymer (e.g., PLGA) chains break up, the cysteamine can diffuse out of the initial polymer microparticle matrix where it will eventually reach the thermoresponsive gel matrix. Diffusion through the thermoresponsive gel is significantly faster than degradation of the polymer. Thus the limiting factor in cysteamine release is degradation of the polymer. In some embodiments, it was unexpectedly discovered that release of cysteamine from spray-dried microparticles comprising PLGA was twice as great when the spray-dried microparticles were dispersed in a PNIPPAAm thermoresponsive gel.

In some embodiments, the spray-dried microparticles comprise 10-20 wt % cysteamine free base and 80-90 wt % PLGA. Thus, each milligram of the microparticles includes 0.1-0.2 mg, or 100-200 µg, cysteamine free base. In certain embodiments, the spray-dried microparticles comprise 15-25 wt % cysteamine hydrochloride and 75-85 wt % PLGA. When the microparticles comprise cysteamine HCl, each milligram of microparticles includes 0.15-0.25 mg, or 150-250 µg, cysteamine HCl. In some embodiments, each milligram of the spray-dried microparticles in the ocular delivery system (microparticles/thermoresponsive gel) releases from at least 60% of the cysteamine HCl over a time period of eight hours. In certain embodiments, each milligram of the spray-dried microparticles in the ocular delivery system (microparticles/thermoresponsive gel) releases from 60-100% of the cysteamine HCl over a time period of 24 hours.

A therapeutically effective dose of cysteamine may be within a range of 20-250 µg per day, with 200 µg per day being a typical dose for an adult human. The ocular delivery system is formulated such that each dose will release a therapeutically effective amount of cysteamine each day.

The ocular delivery system may be administered in the form of a liquid eye drop. In some embodiments, the liquid eye drop has a volume of 25 µL to 75 µL, such as 40 µL or 50 µL.

In certain embodiments, the ocular delivery system is formulated for daily administration and comprises from 0.001 to 0.5 mg spray-dried microparticles per microliter of the ocular delivery system, such as 0.005-0.3 mg, 0.01-0.2 mg, or 0.05-0.15 mg microparticles per microliter of the ocular delivery system. In some examples, the concentration is 0.1 mg microparticles per microliter of the ocular delivery system. A typical 50 µL dose therefore may include 0.05-25 mg microparticles, such as 0.25-15 mg, 0.5-10 mg, or 2.5-7.5 mg microparticles, with each milligram of microparticles including 100-200 µg cysteamine free base or an equivalent amount of a pharmaceutically acceptable salt, such as 150-250 µg cysteamine HCl. In other embodiments, the ocular delivery system is formulated for less frequent administration, e.g., administration every 2-7 days. In such embodiments, the concentration of spray-dried microparticles in the ocular delivery system is adjusted accordingly. For example, if the ocular delivery system is formulated for administration every two days, the concentration of microparticles in the ocular delivery system may be doubled. If formulated for administration every seven days, the concentration may be increased seven-fold.

The ocular delivery system may be administered to any ocular structure, but is preferably administered to the lower fornix. The eye drops may be self-administered by the subject. The eye drop will conform comfortably to the conjunctival sac and release the loaded cysteamine. The eye drop may be administered on a regimen wherein the interval between successive eye drops is once daily (although in certain embodiments the eye drop may be administered more than once daily or at intervals of greater than one day). At the end of the desired administration period, the gelled member can be removed from the eye (for example, via a tweezer or flushing out). In certain embodiments, the thermoresponsive gel may be biodegradable so that there is no need to remove the gelled member (this embodiment may be most useful for treating an acute condition). This system disclosed herein not only drastically decreases the dosing frequency (thereby increasing the likelihood of patient compliance and recovery/prevention of worsening symptoms), it does so while avoiding clinician involvement for administration by being completely noninvasive.

In some embodiments, the ocular delivery system disclosed herein may include an excipient component, such as effective amounts of buffering agents and/or antioxidants to protect the cysteamine from the effects of ionizing radiation during sterilization. Suitable water-soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents are advantageously present in amounts sufficient to maintain a pH of the system of between about 2 to about 9 and more preferably about 4 to about 8. As such the buffering agent may be as much as about 5% by weight of the total system. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight.

Advantageously, embodiments of the disclosed ocular delivery system provide enhanced stability of the cysteamine compared to conventional cysteamine eye drops. Cysteamine is easily oxidized to inactive cystamine and is sensitive to temperature, light, and oxygen. Cysteamine alone has a degradation rate of about 30% in just one week when stored at 4° C. Similar degradation is seen with commercially available Cystaran® eye drops. In contrast, some embodiments of the disclosed ocular delivery system are stable for at least 30 days, with >99% stability over two weeks.

Process for Making Ocular Delivery Systems for Cysteamine

Embodiments of the disclosed ocular delivery systems include spray-dried cysteamine/polymer microparticles dispersed in a thermoresponsive gel. In some embodiments, the polymer in the microparticles is a biodegradable polymer. Suitable biodegradable polymer include, but are not limited to polyglycolide (PGA), poly(lactic acid) (PLA), or poly (lactic-co-glycolic acid) (PLGA). In certain embodiments, the polymer is PLGA.

The microparticles are formed by spray drying a liquid feedstock comprising cysteamine or a pharmaceutically acceptable salt thereof (e.g., cysteamine hydrochloride) and the biodegradable polymer in a solvent. Unless otherwise specified, the term "cysteamine" hereinafter is interpreted as referring to cysteamine or a pharmaceutically acceptable salt of cysteamine. In some embodiments, the solvent is an organic solvent. Suitable solvents include dichloromethane and dichloromethane/lower alkyl alcohol mixtures. In certain examples, the solvent comprises 10 vol % methanol/90 vol % dichloromethane. The liquid feedstock may comprise up to 45 wt % cysteamine or a pharmaceutically acceptable salt thereof, such 0.1-45 wt %, 0.1-30 wt %, 0.1-20 wt %, 0.1-10 wt %, 0.1-5 wt %, 0.1-3 wt %, 0.2-3 wt %, 0.3-3 wt %, or 0.3-1 wt % cysteamine or a pharmaceutically acceptable salt thereof. In some examples, the liquid feedstock comprises from 0.3-1 wt % cysteamine free base or an amount of a pharmaceutically acceptable salt of cysteamine sufficient to provide 0.3-1 wt % cysteamine. In certain embodiments, the liquid feedstock comprises from 0.5-1.5 wt % cysteamine HCl, such as 0.8-1.2 wt % cysteamine HCl. The liquid feedstock may comprise from 0.5 to 10 wt % of the polymer, e.g., PLGA, PLA, or a combination thereof. In certain examples, the liquid feedstock includes 2-6 wt % PLGA, such as 3-5 wt % PLGA. In some embodiments, the liquid feedstock has a weight ratio of biodegradable polymer to cysteamine within a range of from 0.5 to 100, such as 1 to 50 or 2 to 20. The liquid feedstock may have a total solids content (cysteamine plus polymer) within a range of from 0.6-55 wt %, such as 0.9-25 wt %, 1-12 wt %, 2-12 wt % or 2-7.5 wt %.

The liquid feedstock is directed to a spray-drying apparatus comprising a drying chamber comprising an inlet and an outlet, a nozzle coupled to the inlet, a spray gas source coupled to the nozzle, a separator coupled to the drying chamber outlet, and an aspirator coupled to the separator. In some embodiments, the inlet temperature is within a range of 25-75° C., such as 40-60° C. or 45-55° C. The outlet temperature may be within a range of 30-55° C., such as 30-40° C., 34-45° C., or 34-37° C.

The nozzle may be any suitable nozzle. In some embodiments, the nozzle is a two-fluid nozzle through which the liquid feedstock and a spray gas are flowed. In some embodiments, the liquid feedstock is flowed through the nozzle at a flow rate within a range of from 1-5 mL/minute, such as from 2-3 mL/minute. The spray gas may be air or an inert gas (e.g., nitrogen, argon, helium). In some embodiments, the spray gas is nitrogen or air. The spray gas may have a flow rate within a range of 25-500 L/hour. The spray gas atomizes the liquid feedstock as it exits the nozzle, forming droplets of the liquid feedstock. At least a portion of the solvent is removed from the droplets in the drying chamber, thereby forming a plurality of microparticles comprising PLGA and cysteamine. The microparticles are collected by any suitable means. In some embodiments, the microparticles are collected in a separator, such as a cyclone separator, which separates the microparticles from the exhaust gas. The aspirator coupled to the separator may be operated at a flow rate within a range of about 25-35 m³/hour. The collected microparticles may be stored under nitrogen. The collected microparticles may be washed with deionized water prior to storage.

In some embodiments, the spray-dried microparticles comprise a solid dispersion of cysteamine and PLGA in which the cysteamine is dispersed throughout the microparticles. In certain examples, the cysteamine is homogeneously dispersed throughout the microparticles. This dispersion is in stark contrast to similar microparticles prepared by emulsion methods, in which the cysteamine is preferentially localized to the microparticle surface. Emulsion in the presence of relatively high salt concentrations (e.g., NaCl) helps drive cysteamine further into the microparticles, but the high salt content has deleterious effects when the microparticles are incorporated into a thermoresponsive gel matrix.

The thermoresponsive gel may be made from a combination or mixture of any of the thermoresponsive gels disclosed herein. The base precursor (e.g., a prepolymer, oligomer and/or monomer) for the thermoresponsive gel, any cross linkers, and initiators are mixed together and allowed to polymerize for a predefined period of time (from 1 h to 24 h typically) to form the thermoresponsive gel. The thermoresponsive gel is then washed to remove any excess initiator or unreacted materials. The thermoresponsive gel at this stage is a liquid (e.g., in the form of an aqueous solution) at room temperature until it is ready for use. The spray-dried microparticles can be added in before, after, or during the polymerization of the thermoresponsive gel (adding microparticles in before or during polymerization may result in a slighter faster initial drug release rate) to form a suspension of solid microparticles in thermoresponsive gel. In some embodiments, the microparticles and thermoresponsive gel are mixed for 20-30 minutes to provide a homogenous dispersion of the microparticles within the thermoresponsive gel. The amount of microparticles loaded into the thermoresponsive gel may vary. For example, there may be up to 10 mg, such as 0.2-10, 0.2-5, or 0.2-1 mg spray-dried microparticles per microliter thermoresponsive gel. Optional components can be added that allow for easier visualization of the thermoresponsive gel/microparticle suspension such as sodium fluorescein or other fluorescent molecules such as FITC, rhodamine, or AlexaFluors or dyes such as titanium dioxide. The water content of the swollen thermoresponsive gel at room temperature may be 50-80 wt %. The water content of the thermoresponsive gel after it gels in situ in the eye may be 1-10 wt %.

In some embodiments, addition of poly(ethylene glycol) PEG (400 Da) enables the drop to be opaque (and therefore easily visible with the naked eye) and firm enough to be removed with tweezers. In certain embodiments, the amount of PEG added and the molecular weight of PEG are varied to lower the phase transition temperature closer to an ideal value of 27° C. (as low as possible while still being sufficiently above room temperature).

The invention will be further described in the following examples, which do not limit the scope of the invention described in the claims.

EXAMPLES

Example 1: Synthesis and Characterization of Cysteamine/PLGA Microparticles and Thermoresponsive Gel Formulations A liquid feedstock including 1 wt % cysteamine hydrochloride, 4 wt % PLGA (Resomer® RG 752 H PLGA (lactide:glycolide 75:25, Mw 4,000-15,000 Da), Evonik), and 95 wt % of 10 vol %/methanol/90 vol % dichloromethane was prepared. A Buchi B290 spray dryer was used to dry the feedstock. The aspirator was set at 80% (~28 m³/hr) and the inlet temperature was set at 55° C. The feedstock flow rate was set at 10% (2.5 mL/minute). The spray gas flow rate was 40 L/hr. The outlet temperature was 37° C. As shown in FIG. 2, spherical microparticles were obtained.

In another example, a similar liquid feedstock including 2.064 g cysteamine hydrochloride, 8.055 g PLGA (Resomer® RG 752 H PLGA), and 190.19 g of 10 vol % methanol/90 vol % dichloromethane was prepared. A Buchi B290 spray dryer was used to dry the feedstock. The aspirator was set at 100% (~35 m³/hr) and the inlet temperature was set at 45° C. The feedstock flow rate was set at 10% (2.5 mL/minute). The spray gas flow rate was 473 L/hr. The outlet temperature was 32-34° C. over the course of the spray drying process. After spray drying was complete, 0.5161 g of product was recovered from the collection vessel, 0.513 g of product was collected from the upper portion of the cyclone separator, and 1.209 g of product was collected from the lower portion of the cyclone separator. As shown in FIG. 3, spherical microparticles were obtained.

Figure 4:
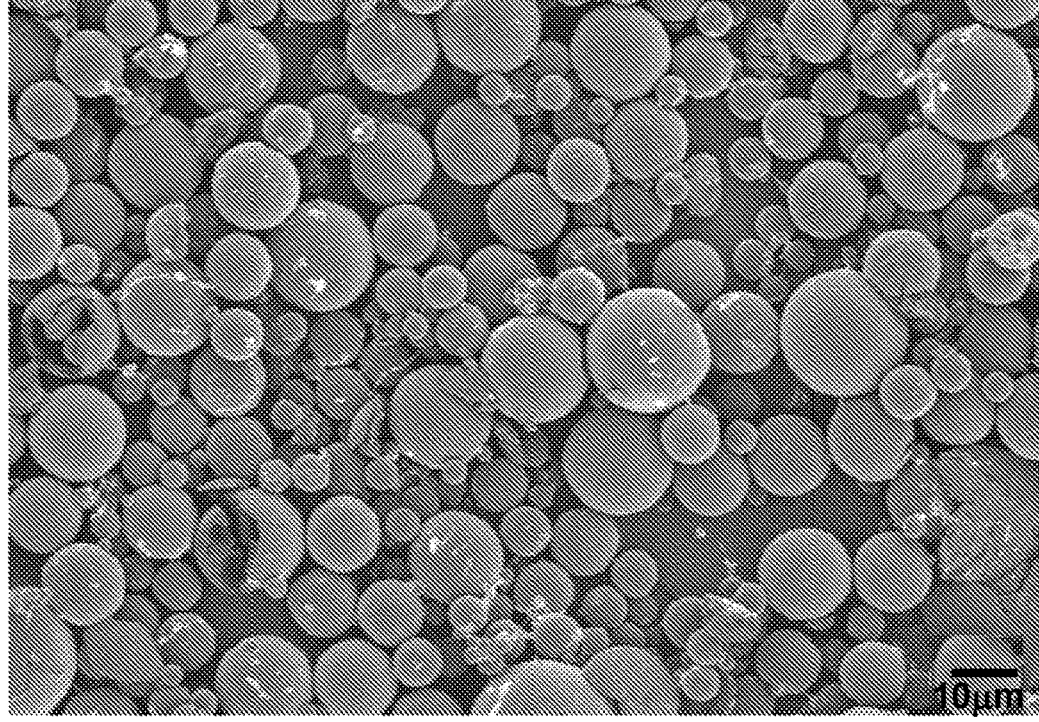
FIG. 4 is an SEM image of cysteamine hydrochloride/PLGA microparticles obtained by a double emulsion method.

Drug release from the spray-dried cysteamine HCl/PLGA microparticles (SD-CMS) was compared to drug release from cysteamine HCl/PLGA microparticles prepared by a standard double emulsion method as described elsewhere (see, e.g., Sanchez et al., *Int. J. Pharmaceutics*, 99(2-3):263-273 (1993); and Zweers et al., *J. Control Release*, 114(3): 317-324 (2006)) and washed with NaCl (DE-CMS-NaCl) prior to storage in nitrogen. NaCl was discovered to increase the cysteamine loading in the DE-CMS particles by driving the cysteamine into the microparticles; in the absence of the NaCl wash, cysteamine was preferentially located on the surface of the microparticles. FIG. 4 is an SEM image of cysteamine HCl/PLGA microparticles prepared by the double emulsion method. Although spherical microparticles were obtained, the microparticles were about 5-10 times larger and were markedly less porous than the microparticles obtained by spray drying (FIGS. 2-3).

Drug release was determined in vitro. Known masses of particles were suspended in the phosphate buffered saline and incubated at 37° C. The microparticle suspensions were centrifuged after predetermined intervals of time and the supernatant was removed for analysis. Released cysteamine was detected by derivatization with CMQT (2-chloro-1-methylquinolinium tetrafluoroborate, followed by HPLC separation and UV/Vis spectroscopy. The HPLC separation utilized a gradient elution of a mobile phase of A—trichloroacetic acid pH 2.0, and B—acetonitrile: t=0-9 minutes B=12% t=9-12 minutes B=30%, t=15-20 minutes B=80%; a Zorbax® SB C-18 column (Agilent Technologies) was used. Absorbance was measured at 370 nm. Other columns and/or solvents also may provide separation and subsequent detection.

CMQT

Cysteamine $$\xrightarrow[\text{-HCL}]{\text{pH} = 7-7.5}$$

Cysteamine-CMQT Derivative

Figure 5:
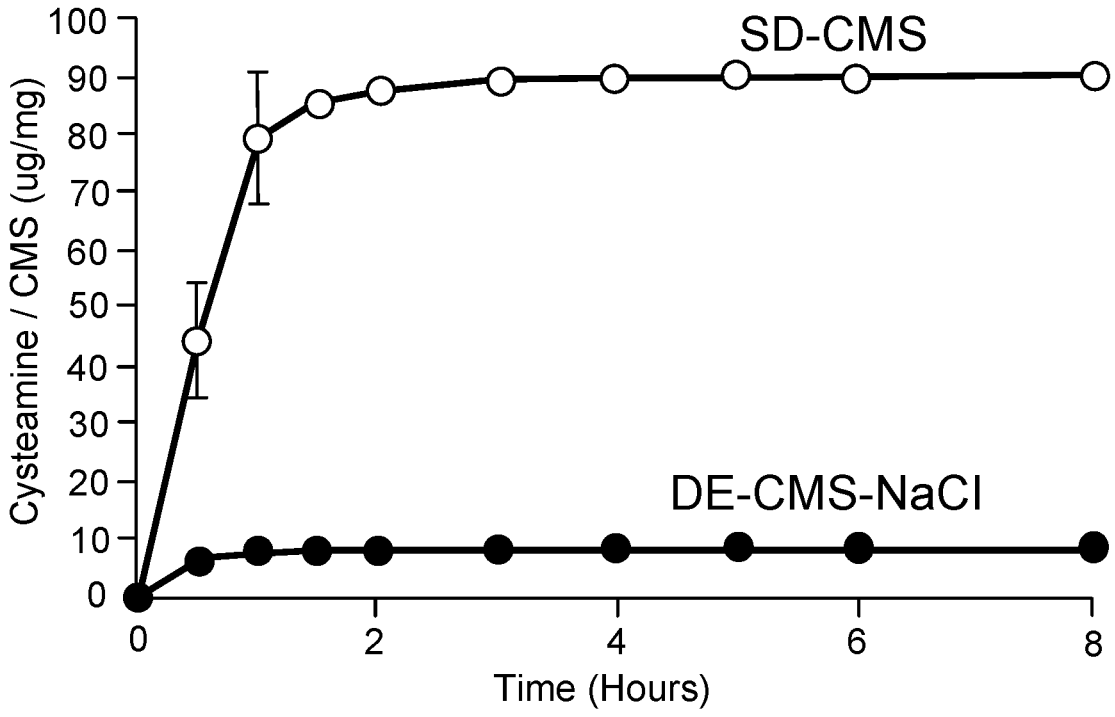
FIG. 5 is a graph showing hourly release kinetics of spray-dried cysteamine HCl/PLGA microparticles as disclosed herein compared to cysteamine HCl/PLGA microparticles prepared by a double emulsion method.

As shown in FIG. 5, the hourly release kinetics were far superior with the spray-dried microparticles having an increased drug loading and a release of cysteamine more than 9-fold greater than the microparticles formed by the double emulsion method.

Figure 6:
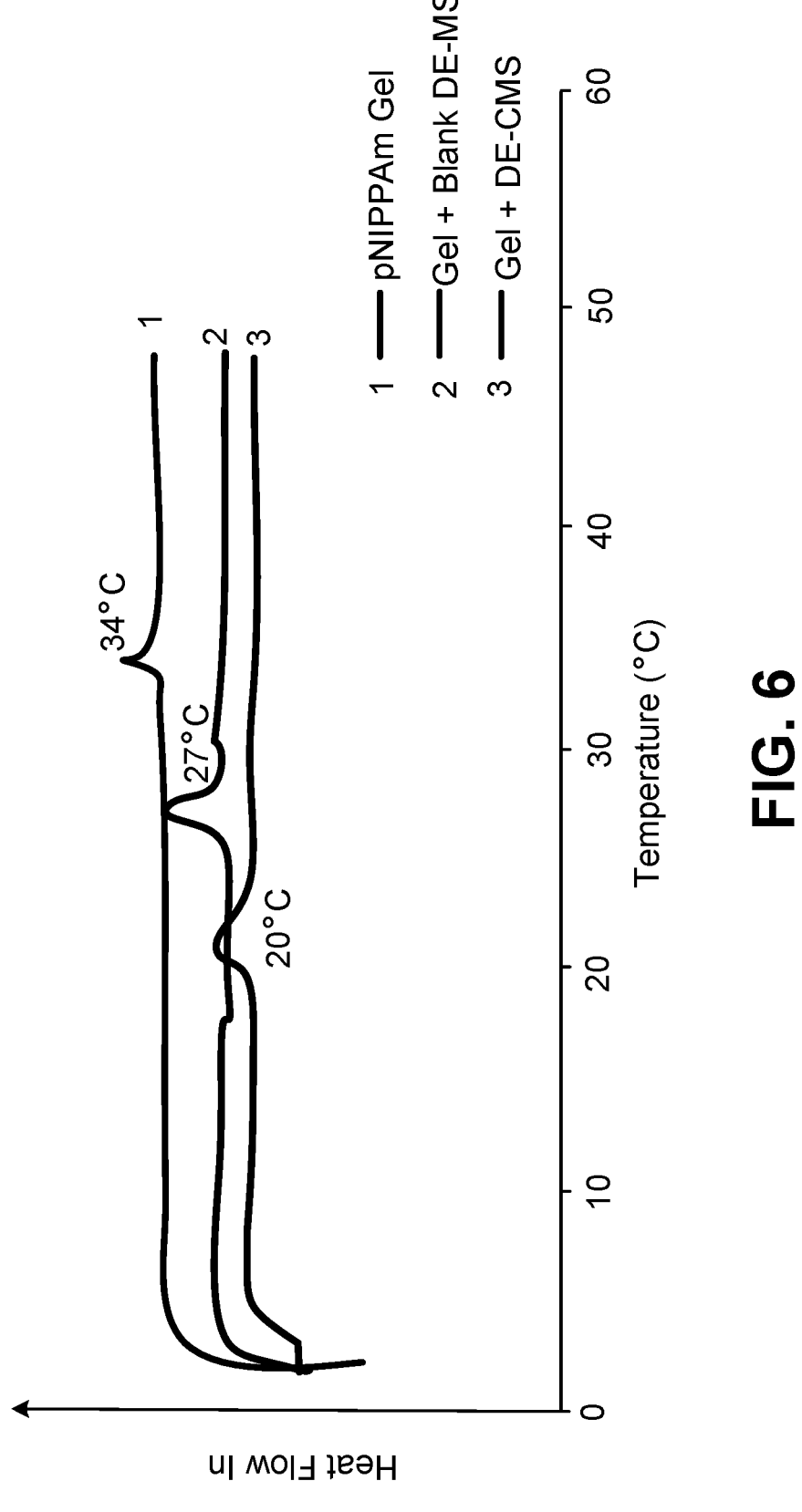
FIG. 6 is a graph showing the phase transition temperature for PNIPAAm thermoresponsive gel alone, with PLGA microparticles formed by a double emulsion method, and with cysteamine HCl/PLGA microparticles formed by the double emulsion method.
Figure 7:
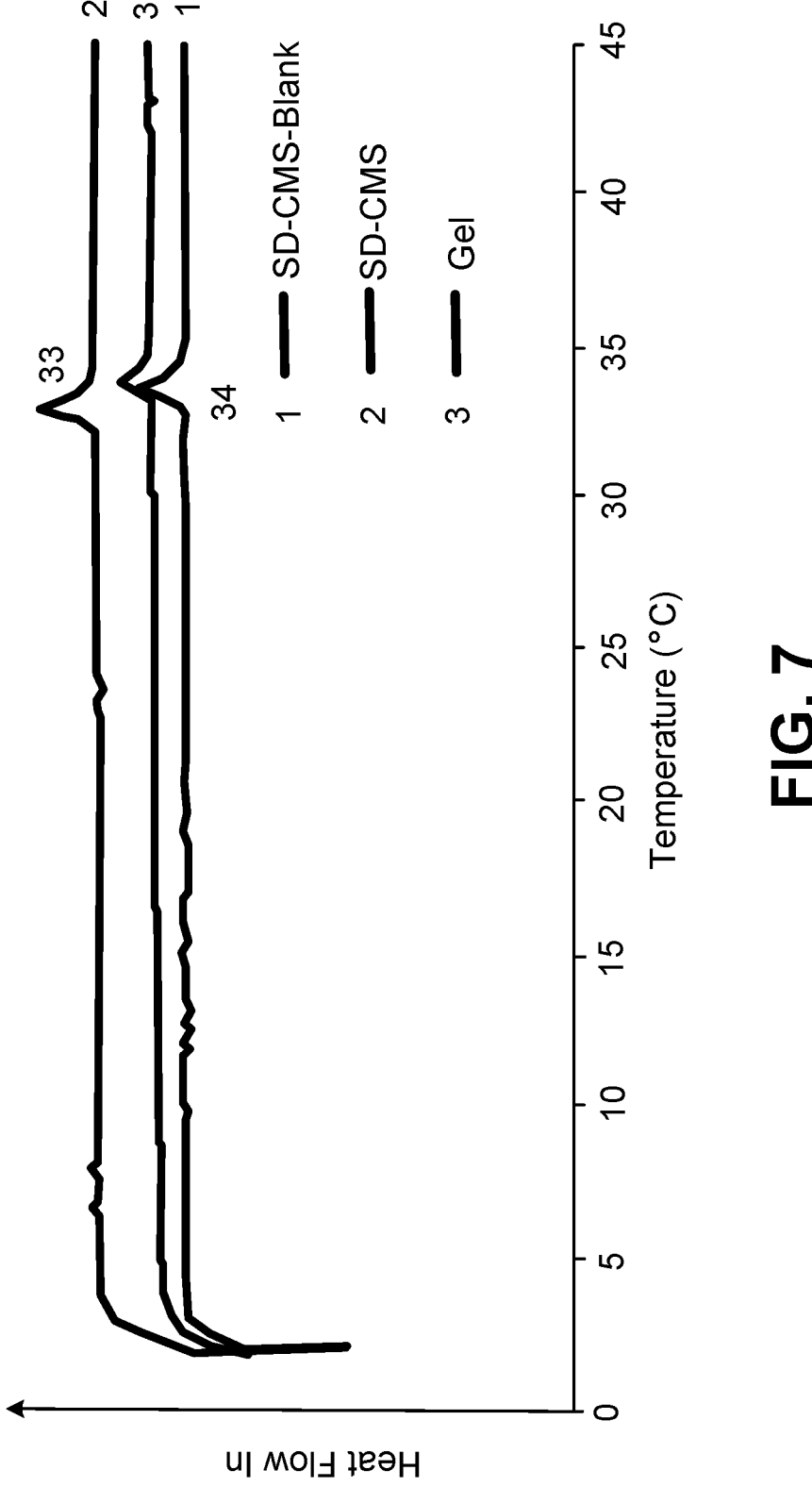
FIG. 7 is a graph showing the phase transition temperature for PNIPAAm thermoresponsive gel alone, with PLGA microparticles formed by spray drying as disclosed herein, and with cysteamine HCl/PLGA microparticles formed by spray drying as disclosed herein.

The SD-CMS particles were suspended in a PNIPAAm thermoresponsive gel matrix, and the effects on the phase transition temperature (LCST) were evaluated and compared to microparticles formed by a double emulsion method. In each case, the concentration was 100 mg particles per 100 μL PNIPAAm thermoresponsive gel matrix. As shown in FIGS. 6 and 7, the PNIPAAm gel alone has an LCST of 34° C. Addition of PLGA microparticles formed by a double emulsion method (blank DE-MS) and washed with NaCl reduced the LCST to 27° C., and addition of cysteamine HCl/PLGA microparticles prepared by the double emulsion method (DE-CMS) reduced the LCST even further to 20° C. (FIG. 6), resulting in solidification of the formulation at room temperature. In contrast, when spray-dried PLGA microparticles (SD-CMS-Blank) or spray-dried cysteamine HCl/PLGA microparticles (SD-CMS) were added to the gel, the LCST remained substantially the same at 33° C. (FIG. 7).

Figure 8:
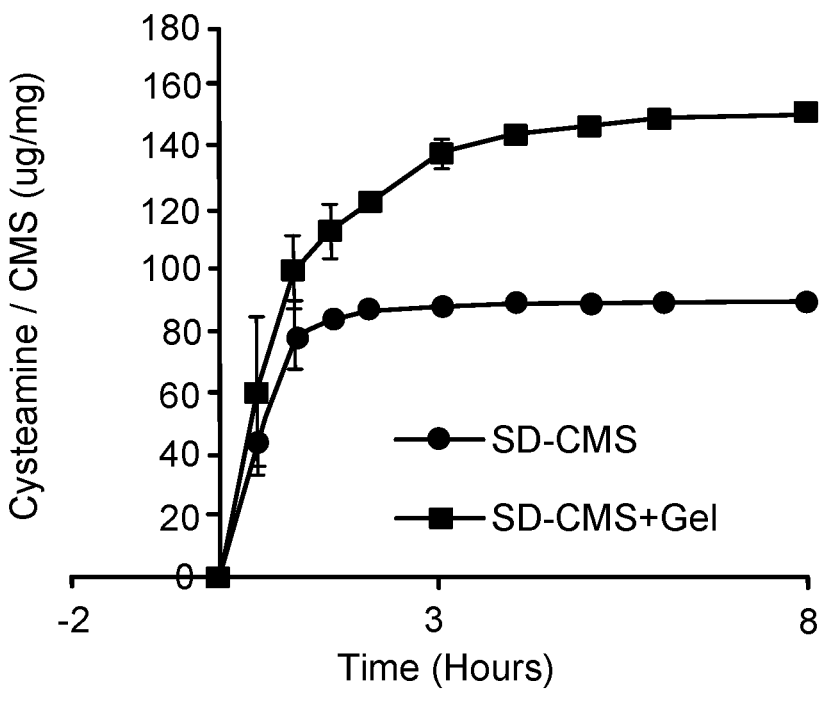
FIG. 8 is a graph showing the hourly release kinetics of spray-dried cysteamine HCl/PLGA particles dispersed in a PNIPAAm thermoresponsive gel matrix compared to the spray-dried cysteamine HCl/PLGA particles alone.
Figure 9:
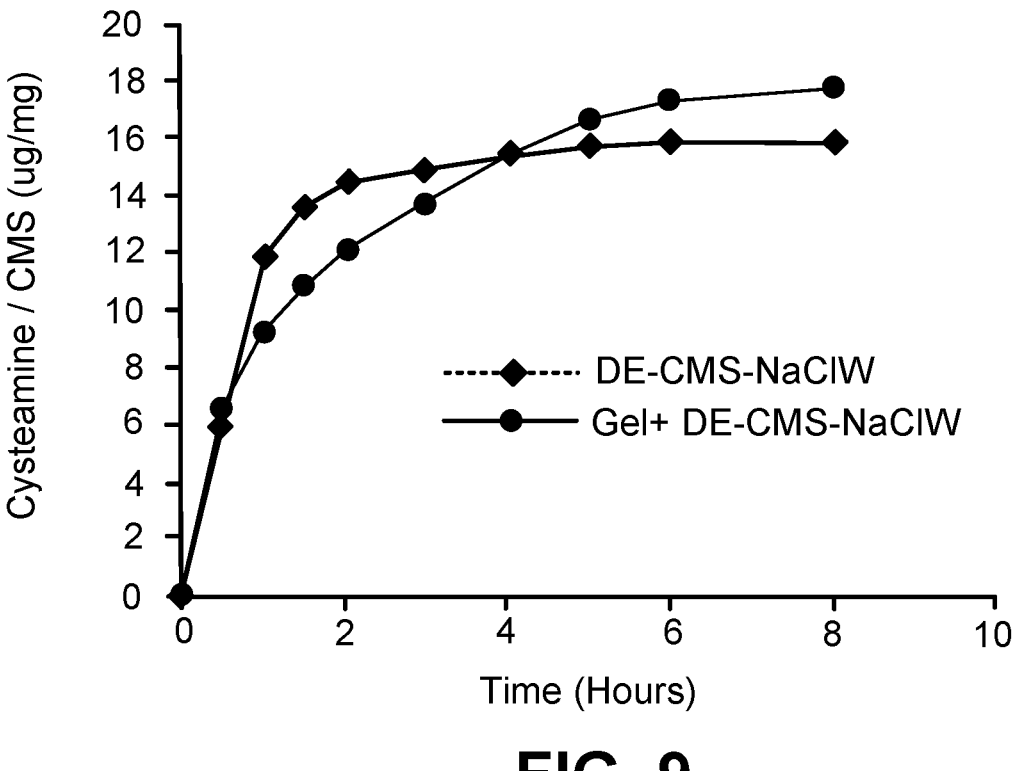
FIG. 9 is a graph showing the hourly release kinetics of cysteamine HCl/PLGA particles prepared by double emulsion and dispersed in a PNIPAAm thermoresponsive gel matrix compared to the cysteamine HCl/PLGA particles alone over 8 hours.

Drug release from SD-CMS particles suspended in a PNIPAAm thermoresponsive gel matrix was evaluated and compared to drug release from the SD-CMS particles alone. The formulation included 10 mg SD-CMS particles per 100 μL of the PNIPAAm thermoresponsive gel matrix. Unexpectedly, the SD-CMS particles suspended in the thermoresponsive gel matrix released approximately twice as much cysteamine over 8 hours (~160 μg cysteamine per mg of SD-CMS particles) compared to the SD-CMS particles alone (FIG. 8). In contrast, drug release from DE-CMS microparticles (prepared by double emulsion) did not change substantially when the microparticles were suspended in a PNIPAAm thermoresponsive gel matrix (FIG. 9). Moreover, the drug release from the SD-CMS/thermoresponsive gel formulation was about 9-fold greater than the drug release from the DE-CMS/thermoresponsive gel formulation, which was about 18 μg cysteamine per mg of DE-CMS particles.

Figure 10:
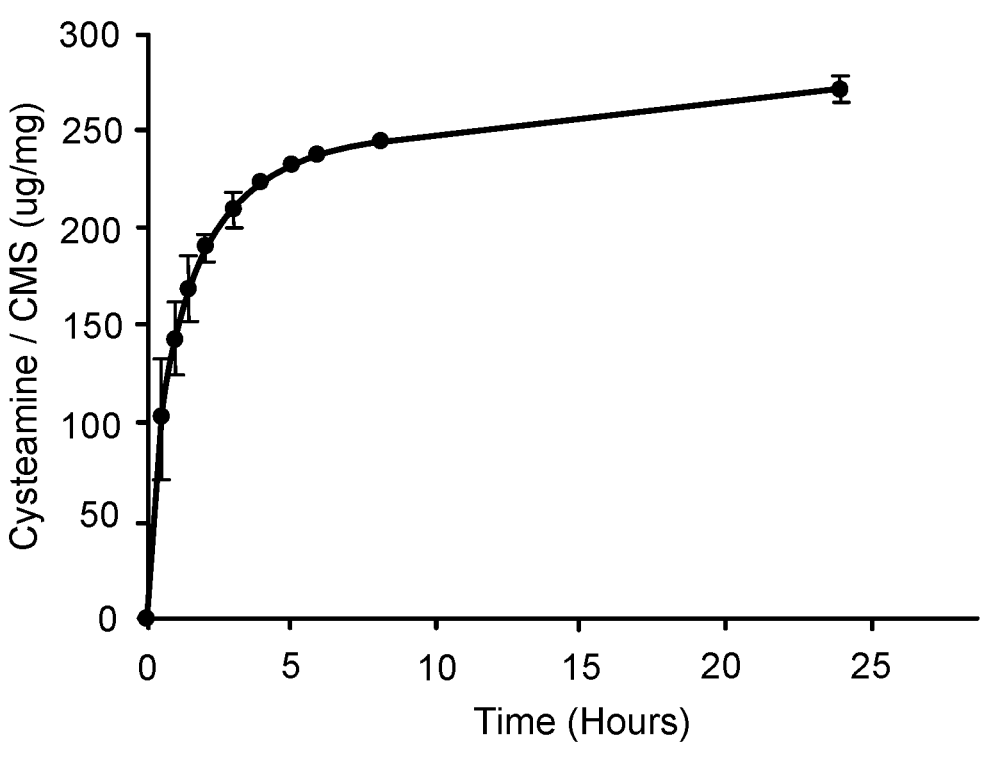
FIG. 10 is a graph showing the hourly release kinetics of spray-dried cysteamine HCl/PLGA particles dispersed in a PNIPAAm thermoresponsive gel matrix over 24 hours.

FIG. 10 shows the drug release from SD-CMS particles suspended in a PNIPAAm thermoresponsive gel matrix (10 mg SD-CMS particles per 100 μL thermoresponsive gel) over a time period 24 hours. Release continued over 24 hours, with ~270 μg cysteamine released per mg of SD-CMS particles.

Figure 11:
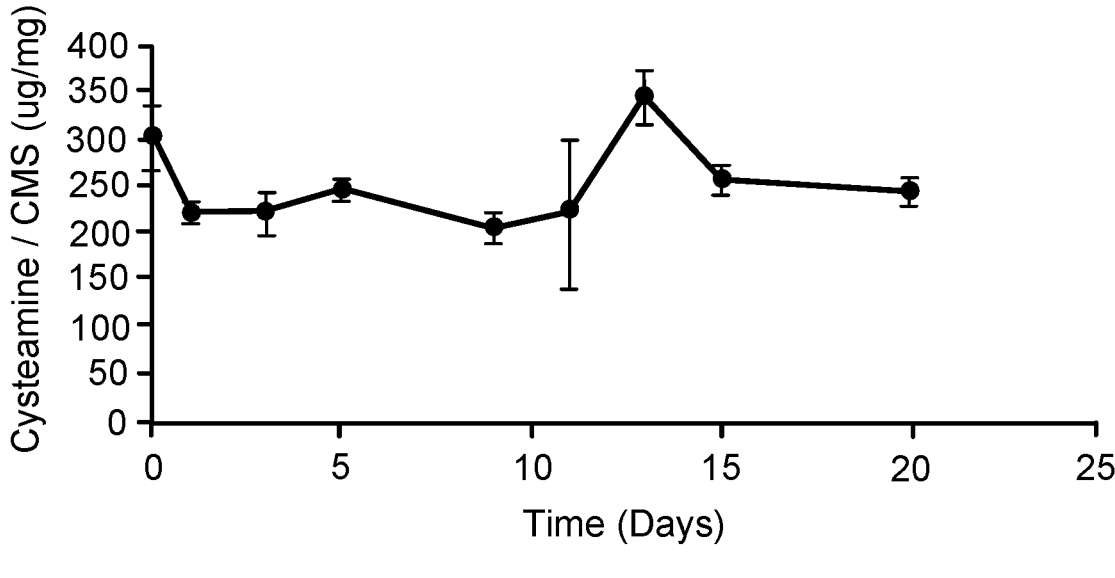
FIG. 11 is a graph showing the stability of cysteamine HCl in spray-dried cysteamine HCl/PLGA particles stored at 4° C.

Embodiments of the disclosed ocular delivery systems comprising cysteamine/PLGA microparticles were stable for at least 20 days. Spray-dried cysteamine/PLGA microparticles were stored at 4° C. and periodic determinations of remaining cysteamine content were made. Stability was determined by CMQT derivatization followed by HPLC separation and UV/Vis spectroscopy as previously described. As shown in FIG. 11, the cysteamine content remained stable with at least 85% remaining after 20 days.

Example 2: In Vivo Efficacy Studies

The disclosed ocular delivery system may be evaluated in CTNS-/- mice, an established model for studying cystinosis. Deletion of the cystinosis gene causes formation of corneal cystine crystals, neovascularization, and scarring in the cornea of ctns transgenic mice, mimicking cystinosis in humans.

Figure 12A:
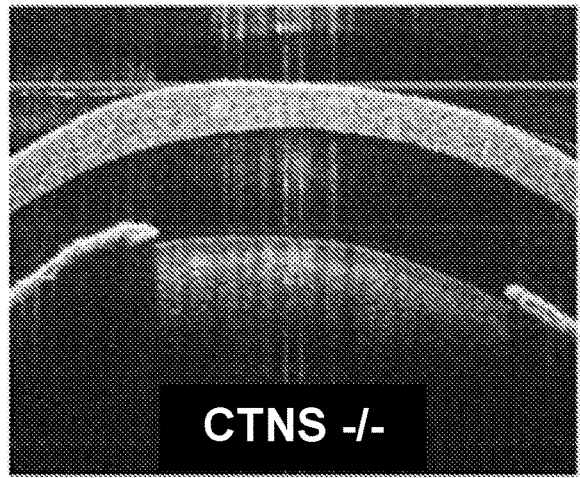
FIGS. 12A and 12B are optical coherence tomography (OCT) images of an eye from a CTNS−/− mouse showing cystine crystals in the cornea (FIG. 11A) and an eye from a control mouse without cystinosis (FIG. 11B).
Figure 12B:
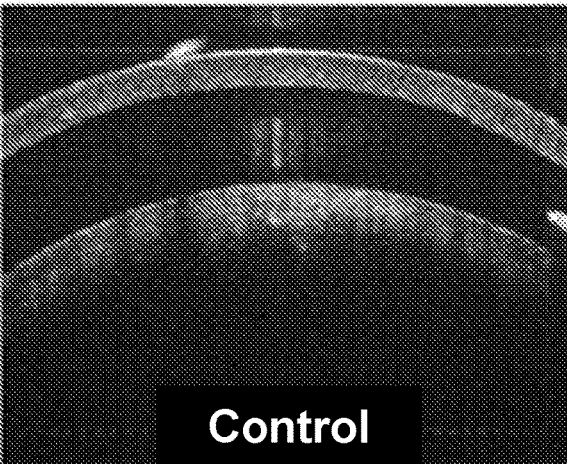

One drop of the ocular delivery system is administered daily to the lower fornix of the eye. On day two and subsequent days, the prior administered gelled formulation is removed before administering the drop. After a predetermined period of time, the eyes are enucleated and examined using optical coherence tomography (OCT) imaging. FIGS. 12A and 12B are OCT images of an untreated eye from a CTNS−/− mouse showing cystine crystals in the cornea (FIG. 12A) and an eye from a control mouse without cystinosis (FIG. 12B). Efficacy of the ocular delivery system will be determined by a reduction in the amount of cystine crystal formation in the treated eye compared to the untreated eye. Alternatively, efficacy may be determined by in vivo confocal microscopy (IVCM) techniques.

Example 3: Cysteamine Release from Cysteamine/PLGA Microparticles and Thermoresponsive Gel Formulations Spray dried cysteamine microspheres (SD-CMS) were fabricated using a Buchi B290 Mini Spray Dryer with a B29F Inert Loop (Buchi New Castle, Delaware, USA). 2 g of cysteamine hydrochloride and 8 g of poly(d-lactic-co-glycolic) acid (PLGA 752H, IV 0.14-0.22 dl/g, Mw: 4,000-15,000) (Evonik Maryland, USA) in a co-solvent consisting of a methanol:dichloromethane (10:90, v/v) solution was used to generate a 5% cysteamine liquid feed. Buchi spray dry process parameters were set as follows: compressed nitrogen, Flow Meter (40 mm), Aspirator (100%), Inlet Temperature (45° C.), Atomizing gas flow (473 L/hour), Feed Rate (10% mL/minute), and Outlet Temperature range (32-35° C.). Samples were collected using a Standard Cyclone and Product Collection Vessel. Cysteamine free microspheres (SD-Blank-MS) were produced using the same fabrication process without the addition of cysteamine hydrochloride.

The shape and morphology of SD-CMS and SD-Blank-MS were examined using scanning electron microscopy (SEM). Samples were gold sputter-coated and imaged using a JEOL 6335F Field Emission SEM (JEOL, Peabody, MA, USA).

Free radical polymerization of pNIPAAM was performed by adding 100 mg of NIPAAm monomer to 2 mL of a 0.5 mg/mL solution of ammonium persulfate (APS) in MilliQ water. 5 μL of tetramethylethylendiamine (TEMED) initiator was added to the solution mixture and stored overnight at 4° C. Excess TEMED and APS were washed from pNIPAAm solution using MilliQ water at repeated cycles of phase transition (above 37° C.). The remaining water and excess reagents were removed by freeze drying with liquid nitrogen and lyophilization for 48 hours. Solid pNIPAAm was obtained and stored at 4° C. A 9.09 wt % (m/m) gel was created by weighing out 0.4713 mg of lyophilized pNI-PAAm and adding 4.71 mL of MilliQ water and 0.470 mL of PEG (avg. MW: 200 kDa) as an excipient. Samples were hydrated over a period of three days with vortexing and centrifugation at 4° C., 1000 RPM (1000G 670 RPM). Samples were stored at 4° C. until use.

After preparation, SD-CMS gel suspensions (SD-CMS/Gel) and SD-Blank-MS gel suspensions (SD-BLANK-MS/Gel) were prepared by weighing out respective microspheres at a ratio of 1 mg:100 μL gel. The lower critical solution temperature (LCST) of gel, SD-CMS/Gel, and SD-Blank-CMS/Gel were determined by DSC. Gel and MS/Gel suspensions were placed in aluminum pans in a Pyris 6 DSC (Perkin Elmer, Waltham, MA USA). Empty aluminum pans were used as reference pans. An initial isothermal hold for 5 minutes at 2.0° C. was implemented prior to heating. After 5 minutes, a temperature scan was performed from 2.00° C.

to 50.0° C. at a heating rate of 2.00° C./minute. A secondary isothermal hold for 2 minutes at 50.0° C. was implemented prior to cooling. After 2 minutes, temperature scan from 50.0° C. to 2.00° C. at a cooling rate of 10.00° C./minute was performed. LCST were determined from resulting DSC curves by extracting peak inflection points (° C.) or the cloud point temperature (Zhang et al., *J. Pharma. Biomed. Anal.*, 146:273-78 (2017)) during the primary heating scan (Heat Flow In).

Cysteamine was detected by derivatizing with 2-chloro-1-methylquinolinium tetrafluoroborate (CMQT) and analyzed with a modified HPLC method (Kusmierek et al., *Biomedical Chromatography*, 22(4):441-45 (2008)). CMQT was synthesized as described elsewhere (Bald et al., *J. Liquid Chromatography &Related Technologies*, 24(9): 1323-39 (2001)). Reduction of reduced cysteamine (cysteamine) with tris(2-carboxyethyl) phosphine hydrochloride (TCEP) was performed prior to CMQT derivatization. Standard cysteamine sample aliquots (100 μL) were placed into 400 μL 0.1 M, pH 7.5 phosphate buffer solution. 20 μL of 0.1 M TCEP was added to the solution mixture, vortexed and reacted for 15 minutes. Immediately after, 20 μL of 0.1 M CMQT was added to the solution mixture, vortexed, and reacted for 5 minutes. The mixture was acidified with 3M hydrochloric acid to terminate the reaction. 20 μL of reaction sample was injected into an autosampler on a 1220 Infinity Liquid Chromatography (Agilent Technologies, California, USA) attached with a 1220 DAD Liquid Chromatography UV detector (Agilent Technologies, California, USA). A reverse-phase Zorbax SD-C18 column (5 μm, 4.6×150 mm, Agilent Technologies, California, USA) was used to separate molecules undergoing a gradient elution. The gradient elution consisted of mobile phases acetonitrile (A) and trichloroacetic acid pH 2.0 (B) at ratios: 0-3 minutes (12% A, 88% B), 3-9 minutes (30% A, 70% B), 9-12 (12% A, 88% B) for 15 minutes at a flow rate of 1.2 mL/minute. The column temperature was held at 25° C. UV Detector was set at 355 nm. Retention times of cysteamine-derivative and excess CMQT were 10.5 minutes and 11.3 minutes, respectively. The column was equilibrated for 5 minutes after each injection. Peak height from cysteamine-derivative were used from standard aliquots to create a standard curve over the range of 1 μg/mL to 50 μg/mL.

Emulsion Based Formulation Preparation

The formulations of cysteamine microspheres (CMS) were fabricated using water/oil/water (W/O/W) double emulsion (CMS1), O/W single emulsion (CMS2), and O/O single emulsion (CMS3) procedures. Briefly, aqueous cysteamine was microemulsified within poly(lactic-co-glycolic acid) (PLGA) in dichloromethane (DCM) for CMS1 and CMS2, while cysteamine in acetonitrile (ACN) was microemulsified in mineral oil and Span-80 for CMS3.

Cysteamine loaded microspheres (SD-CMS) and cysteamine-free microspheres (SD-Blank-MS), along with their corresponding gel suspensions (SD-CMS/Gel, SD-BLANK-MS/Gel) were further characterized for in vitro drug release kinetics over 24 hours. Known masses of SD-CMS were suspended in 0.1M, pH 7.5 phosphate buffer solution (500 μL) in a 1.5 mL Eppendorf tube. Samples were placed in a rotator and incubator at 37° C. For each predetermined time point, samples were spun down at 3500 RPM for 5 minutes, and the supernatant was removed for analysis. Fresh phosphate buffer solution was added to the remaining MS, vortexed, and placed back onto rotator to maintain sink-like conditions. Cysteamine concentrations in phosphate buffer solution were analyzed using an HPLC method. Gel suspension release kinetics were determined similarly, by mixing MS at a ratio of 10 mg:100 µL (MS:Gel) in a 1.5 mL Eppendorf tube, and evaluating with HPLC.

Figure 21:
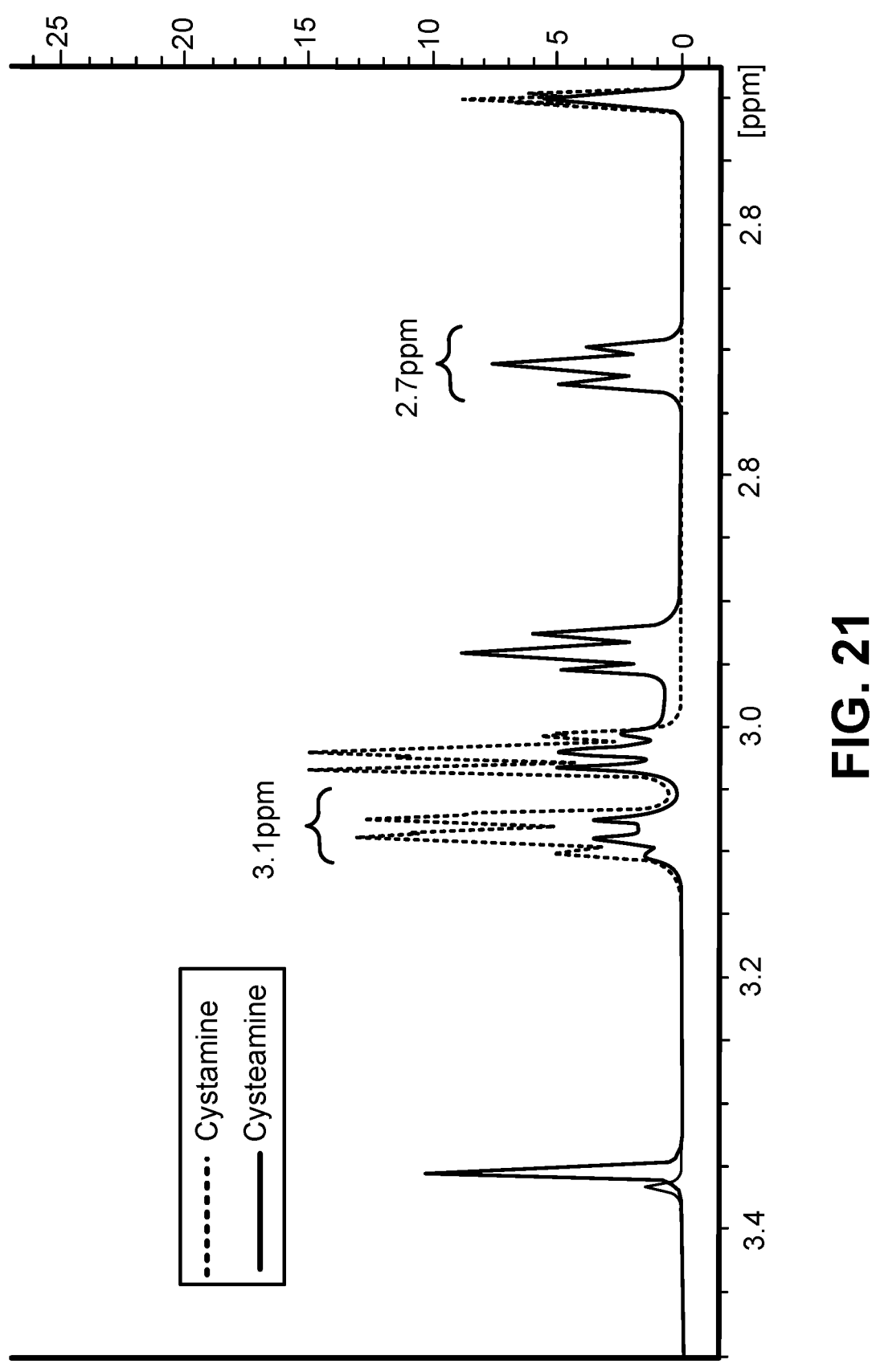
FIG. 21 is NMR spectra resulting in non-overlapping reference peaks of cysteamine (2.7 ppm) and cystamine (3.1 ppm). Cysteamine sample contained cystamine as seen by stacked overlay of cystamine and cysteamine samples at 3.1 ppm.
Figure 22:
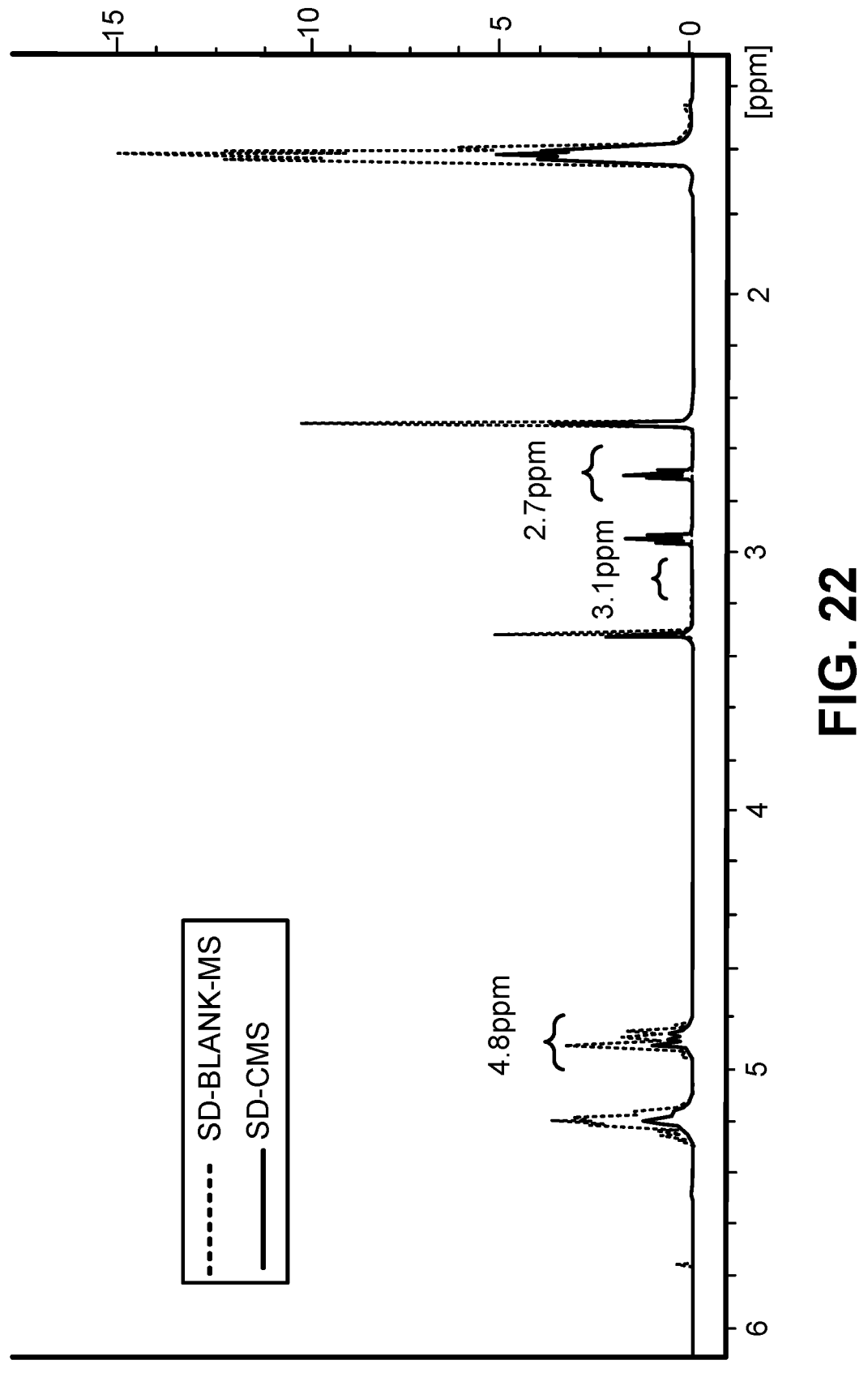
FIG. 22 is full NMR spectra of cysteamine loaded microspheres (SD-CMS) and cysteamine free microspheres (SD-BLANK-MS) resulting in non-overlapping chemical shift peaks of cysteamine (2.7 ppm) and cystamine (3.1 ppm) and PLGA (methylene, 4.8 ppm).

Cysteamine drug loading in PLGA microspheres was quantified using NMR spectroscopy. Reference spectra for PLGA quantification with NRM spectroscopy were implemented (Zhang et al., *J. Pharma. Biomed. Anal.*, 146:273-78 (2017)). The $^1$H-NMR spectra were obtained using a 500 MHz Bruker Avance III spectrometer at 293 K in deuterated dimethyl sulfoxide (DMSO-d6) with a sample concentration of 20 mg/mL. Spectra obtained from 32 scans were calibrated to the residual solvent peak at δ 2.50 ppm and processed with TOPSPIN™ software (Bruker, Billerica, Massachusetts, USA). Reference spectra of cysteamine (FIG. 21), cystamine (FIG. 21), and PLGA (FIG. 22) were utilized as standards, where non-overlapping methylene proton resonances at δ 2.70 ppm (cysteamine), δ 3.10 ppm (cystamine), and δ 4.88 ppm (PLGA) were utilized to determine mass of cysteamine in MS, drug-loading, and % cysteamine according to Equation (Eq.) 1, Eq. 2., and Eq. 3, respectively.

$$\text{Mass of CYS in MS(mg)} = \left( \frac{MM_{CYS} \cdot \frac{J_{CYS}}{P_{CYS}}}{\left( MM_{CYS} \cdot \frac{I_{CYS}}{P_{CYS}} \right) + \left( MM_{PLGA} \cdot \frac{I_{PLGA}}{P_{PLGA}} \right)} \right) \times \text{Mass of MS(mg)} \qquad \text{Eq 1.}$$

Where, $MM_{CYS}$ is the molar mass of cysteamine, 77.15 g/mol, $MM_{PLGA}$ is the molar mass of the PLGA repeat unit "LG", 126.0 g/mol, and/and P are the integral and number of protons, respectively.

$$\text{Drug-loading} \left( \frac{ug}{mg} \right) = \left( \frac{\text{Mass of CYS in MS}(ug)}{\text{Mass of MS(mg)}} \right) \qquad \text{Eq 2.}$$

$$\% \text{ Cysteamine} = \left( \frac{\frac{I_{cysteamine}}{2}}{\frac{I_{cysteamine}}{2} + \frac{I_{cysteamine}}{4}} \right) \times 100 \qquad \text{Eq 3.}$$

Figure 13A:
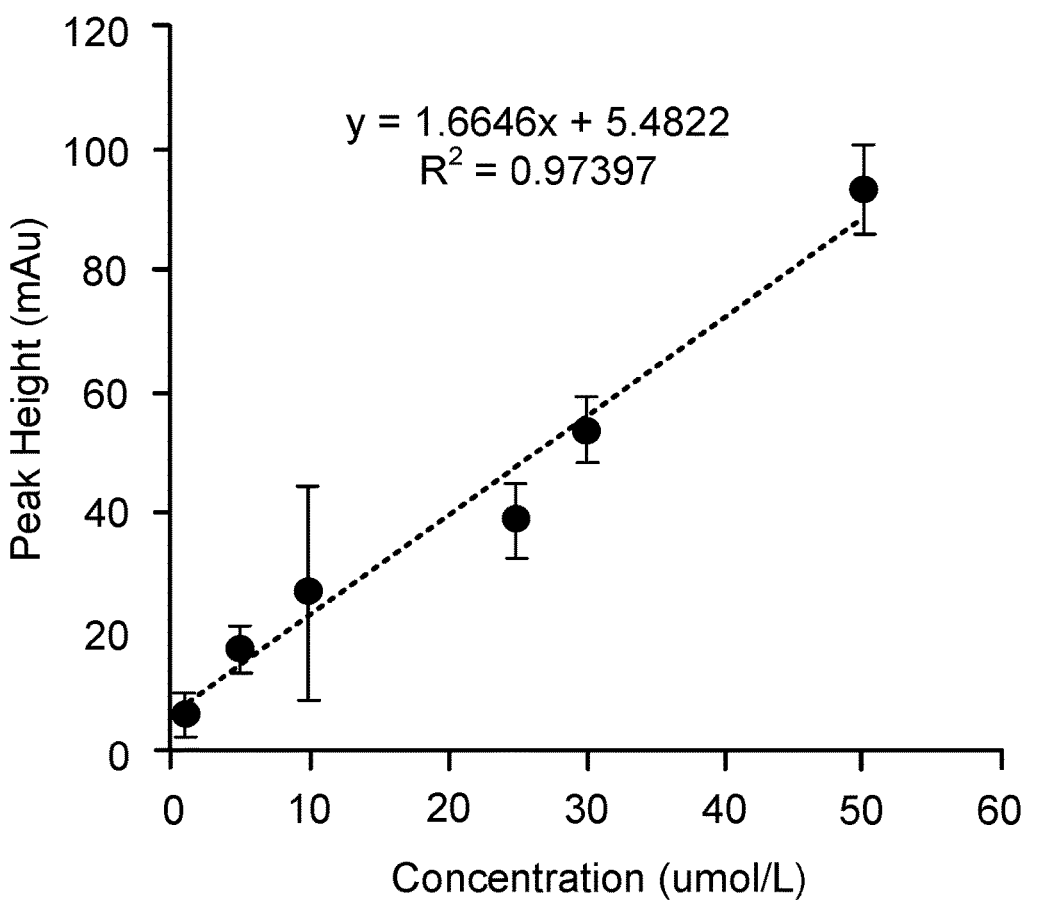
FIGS. 13A and 13B are graphs showing detection of cysteamine using HPLC.
Figure 13B:
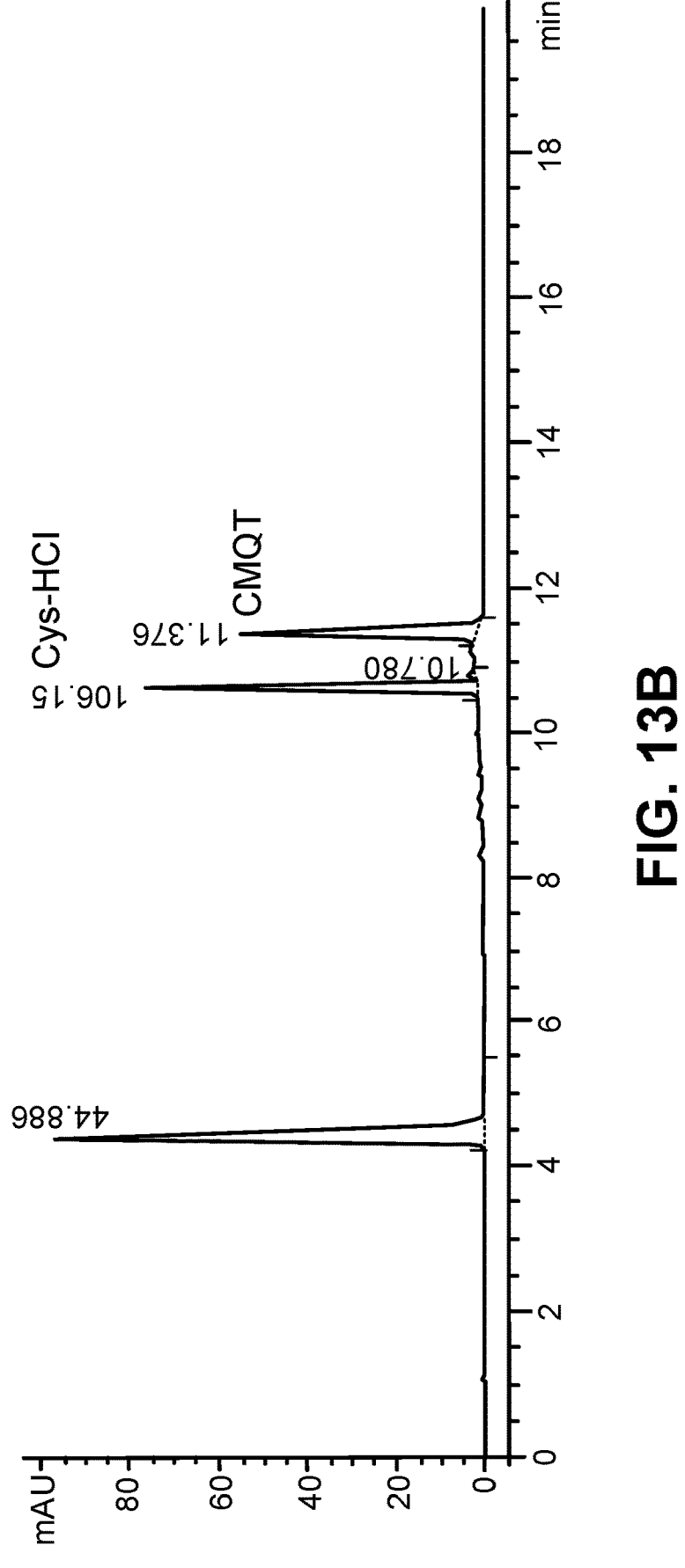

HPLC was used to detect of cystamine/cysteamine alone; released cysteamine/cystamine; and soluble cysteine in vitro. As shown in FIGS. 13A and 13B, HPLC can be used to determine the amount of cysteamine and CMQT, and to distinguish between cysteamine and CMQT.

Figure 14A:
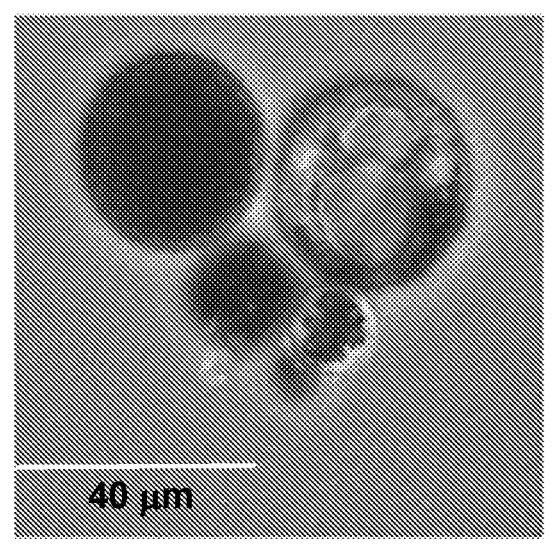
FIGS. 14A and 14B show release of cysteamine from a double emulsion cysteamine microsphere (DE-CMS) formulation.
Figure 14A:
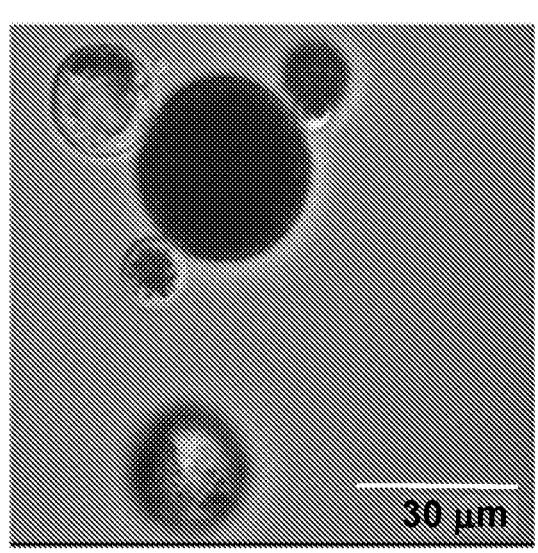
Figure 14B:
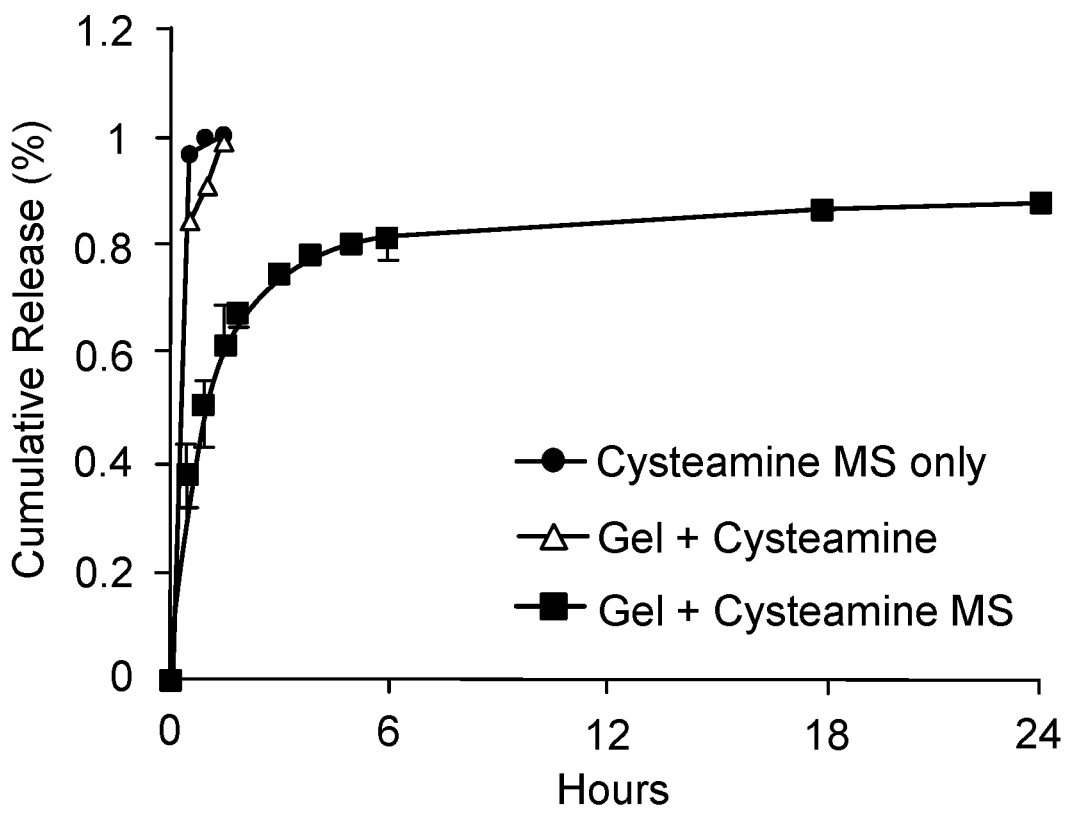

The release of cysteamine from DE-CMS formulations was characterized. FIG. 14A is an image of DE-CMSs. As shown in FIG. 14B, the formulation containing DE-CMSs suspended in a thermoresponsive gel matrix resulted in extended cysteamine release over about 24 hours.

Figure 15A:
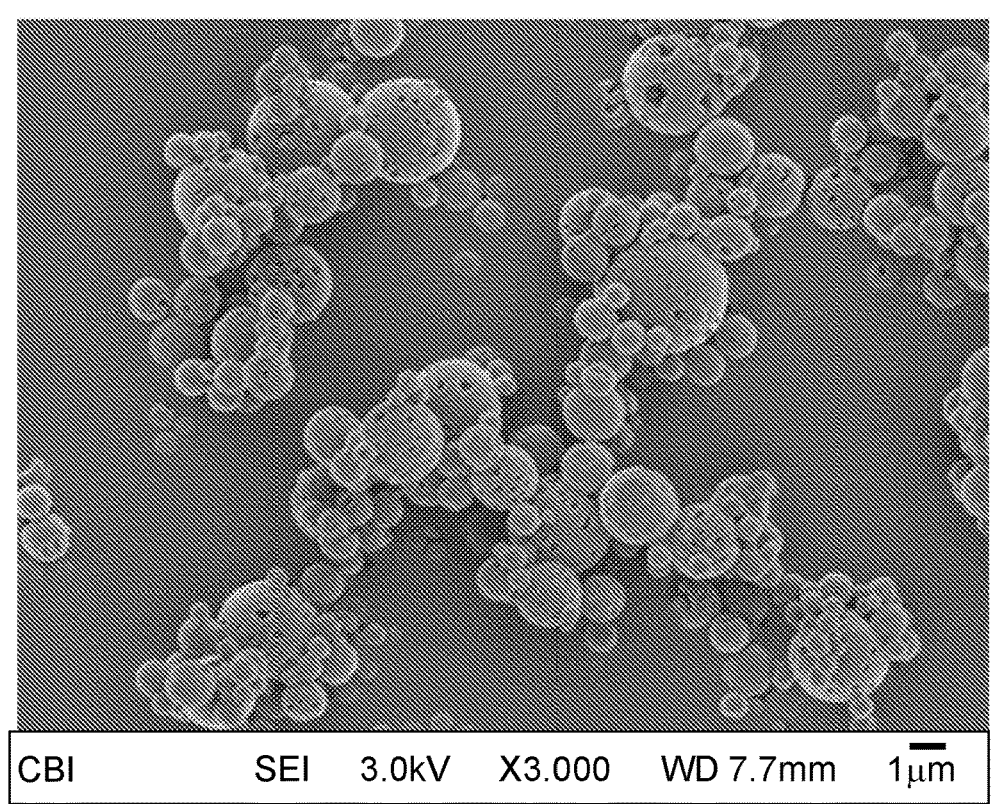
FIGS. 15A and 15B show release of cysteamine from a DE-CMS formulation and from a spray-dried cysteamine microsphere (SD-CMS) formulation.
Figure 15B:
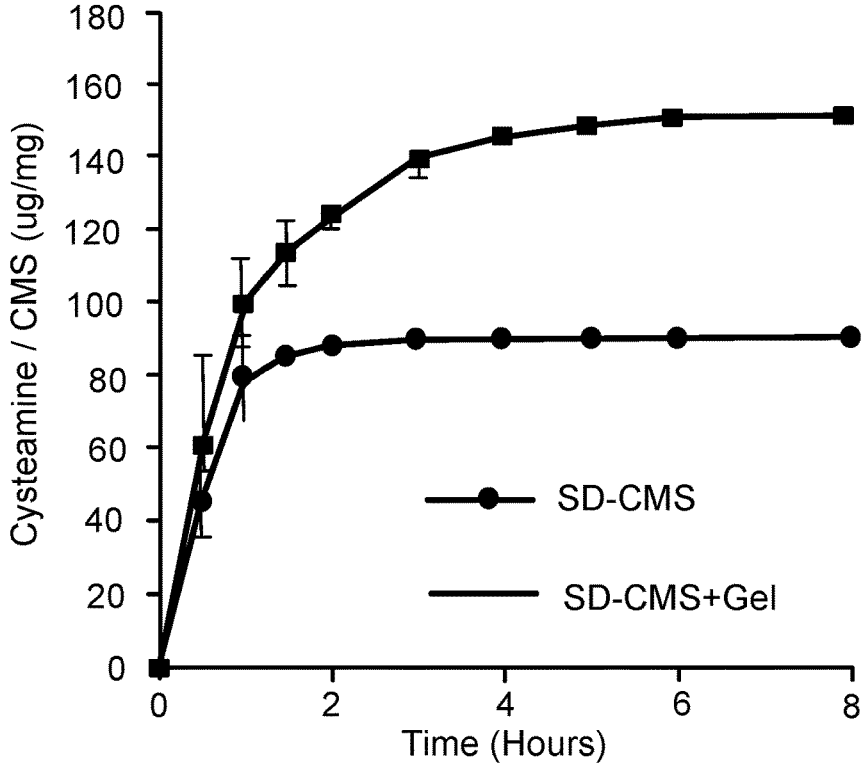

The release of cysteamine from DE-CMS formulations was compared to the release of cysteamine from spray-dried cysteamine microsphere (SD-CMS). FIG. 15A is an image of SD-CMSs. As shown in FIG. 15B, more cysteamine is released from SD-CMSs than from DE-CMSs.

Figure 16:
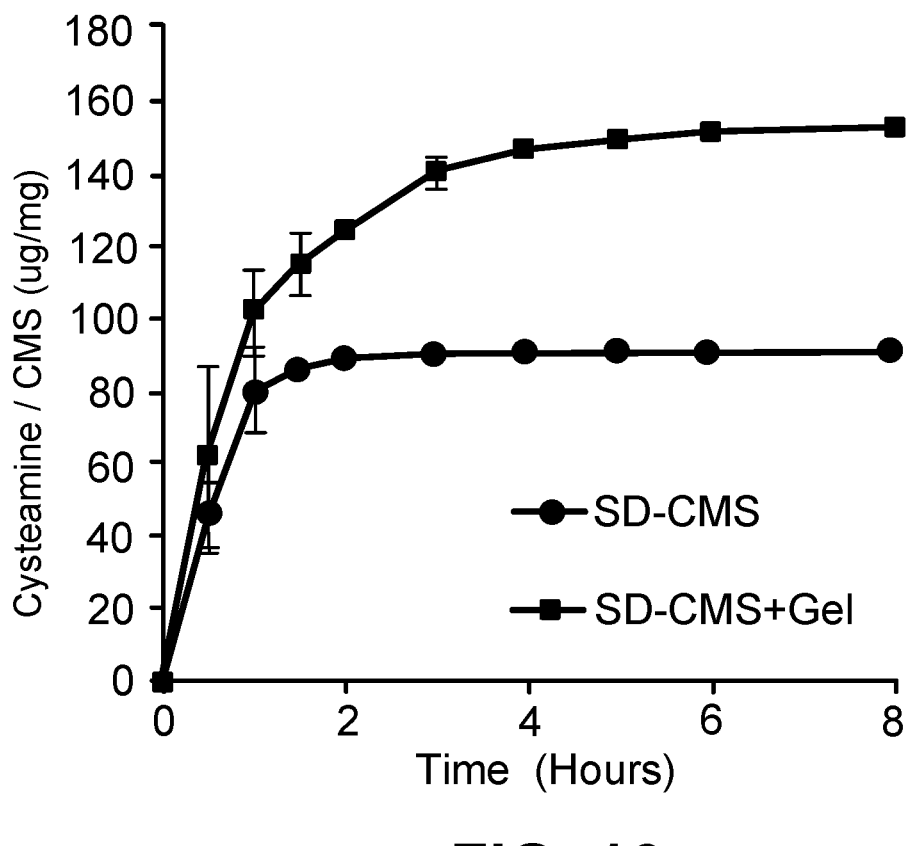
FIG. 16 is a graph showing the release of cysteamine from SD-CMSs suspended in a thermoresponsive gel matrix.

The release of cysteamine from SD-CMSs suspended in a thermoresponsive gel matrix was evaluated. As shown in FIG. 16, SD-CMSs suspended in a thermoresponsive gel matrix resulted in more overall hourly drug release than SD-CMSs that lack a thermoresponsive gel matrix. This release profile suggests that SD-CMSs suspended in a thermoresponsive gel matrix formulation can meet dosing needs for once daily administration of the formulation, and likely even less frequent administration.

Figure 17:
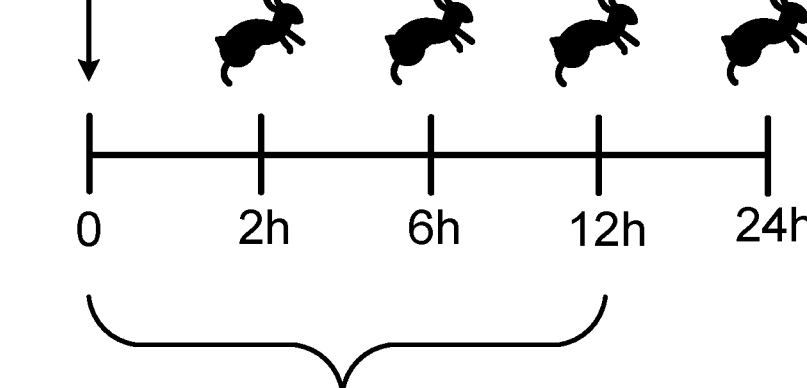
FIG. 17 is a schematic of an exemplary treatment protocol for administering eye drop formulations containing cysteamine microspheres suspended in a thermoresponsive gel to rabbits.

HPLC was also used to detect cysteamine in plasma, aqueous humor, cornea, vitreous in vivo following administration of cysteamine formulations to rabbits (FIG. 17). Cysteamine was detected in the cornea 24 hours after drop administration.

Figure 18A:
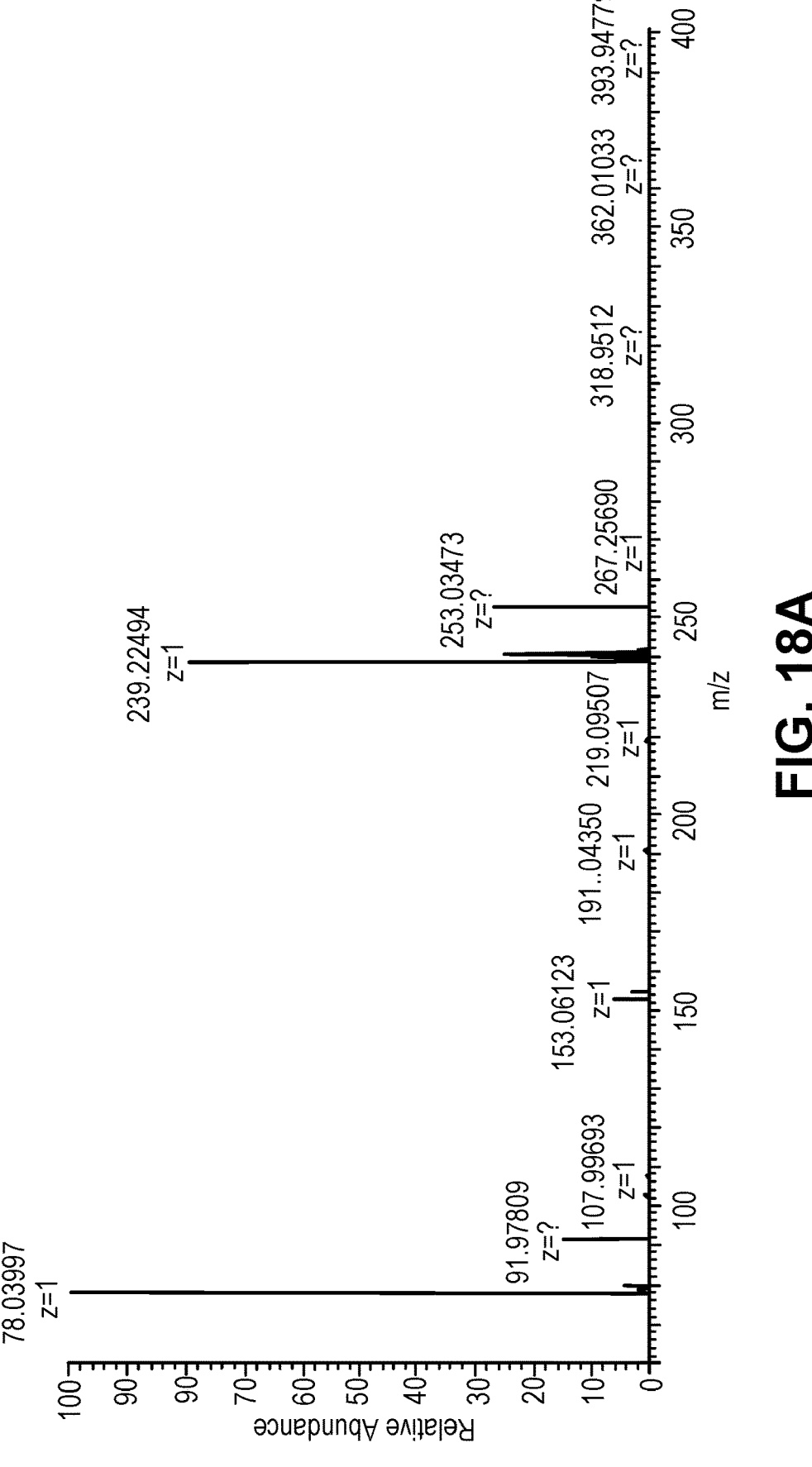
FIGS. 18A, 18B, and 18C shows detection of cysteamine using liquid chromatography-mass spectrometry (LC-MS).
Figure 18B:
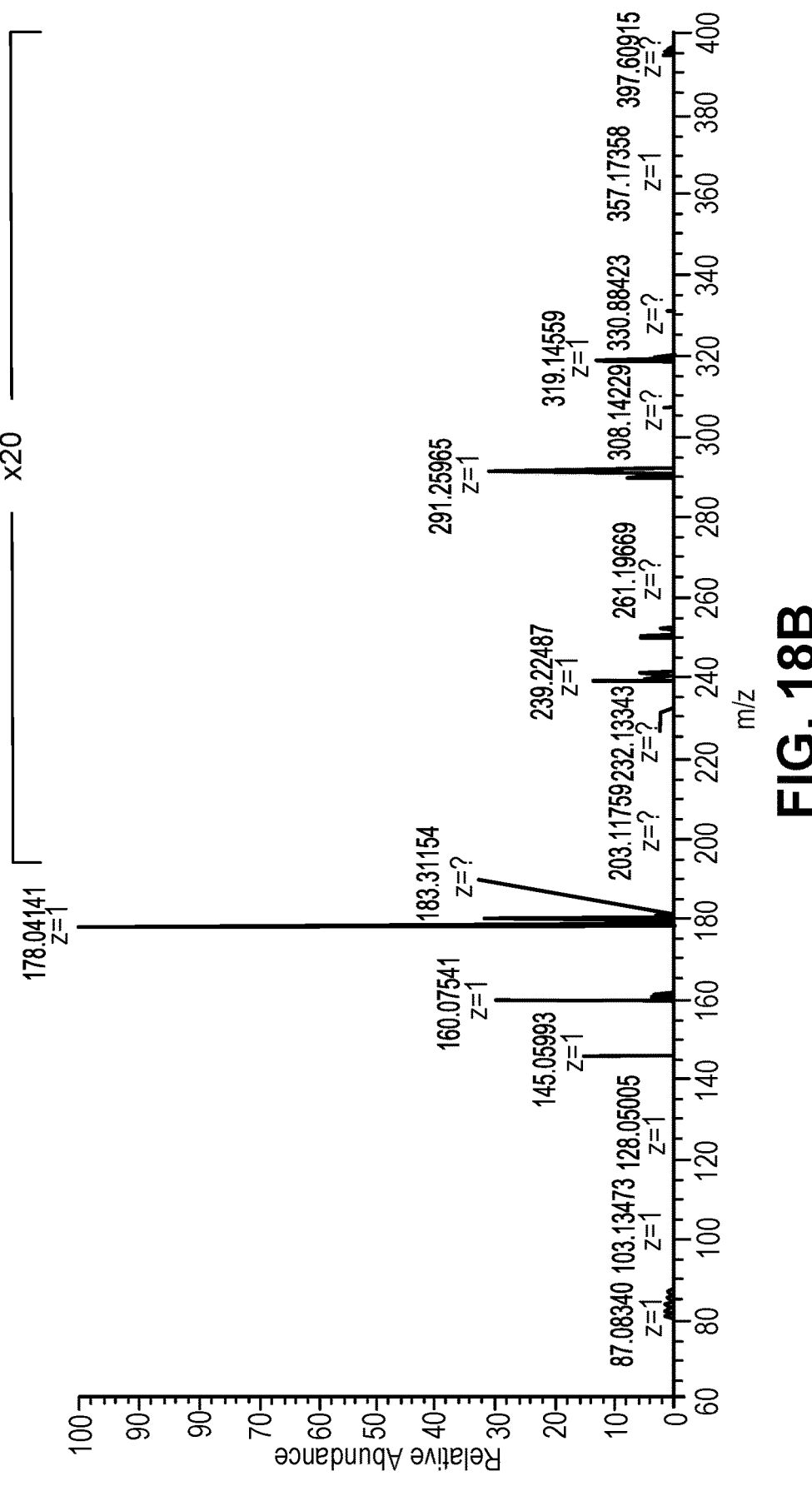
Figure 18C:
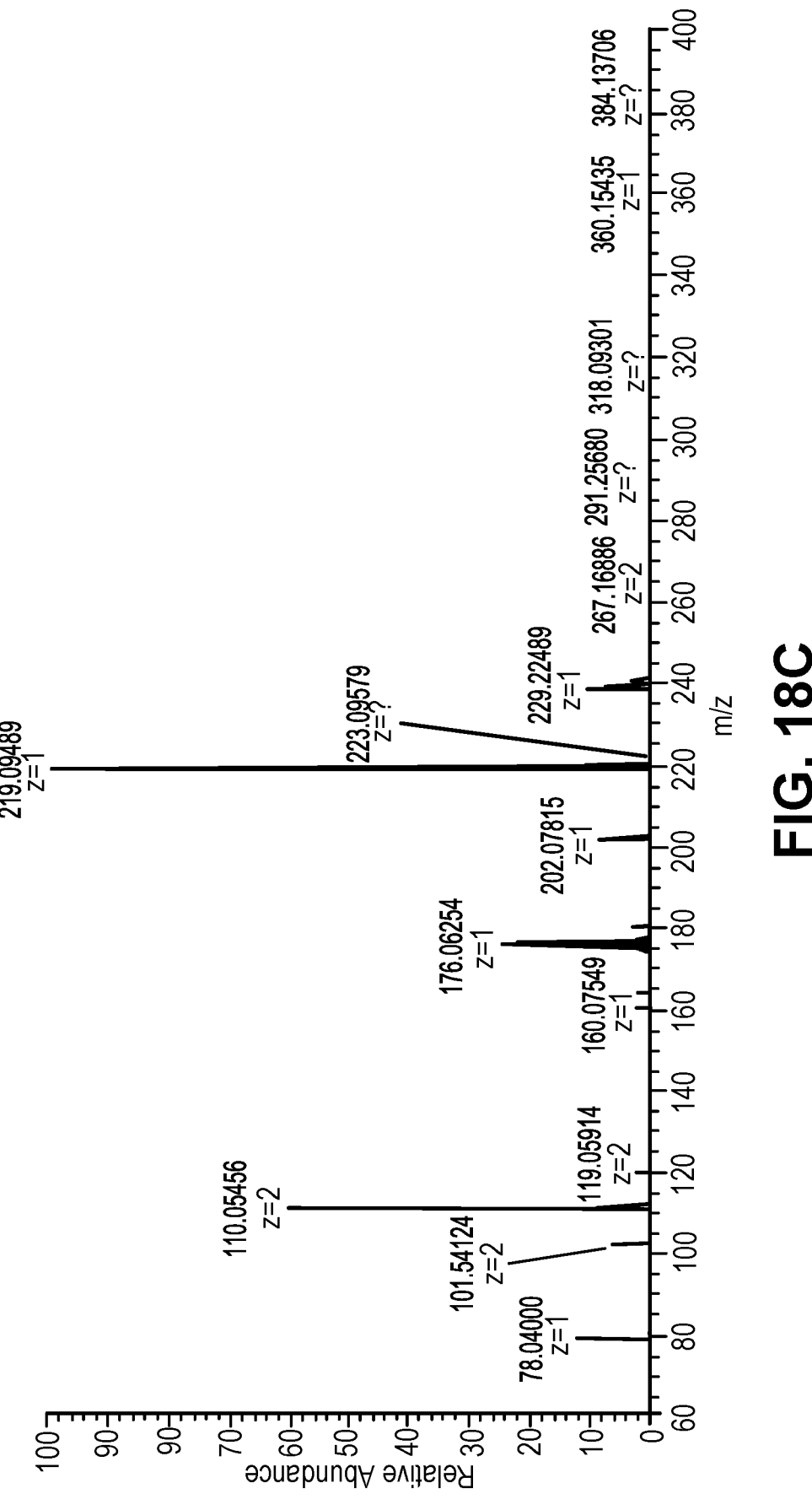

Cysteamine was also detected using liquid chromatography-mass spectrometry (LC-MS). As shown in FIG. 18, LC-MS can be used to detect, and to distinguish between, cysteamine (FIG. 18A), cystamine (FIG. 18A), CMQT (FIG. 18B), and a CMQT-cysteamine derivative (FIG. 18C).

Figure 19:
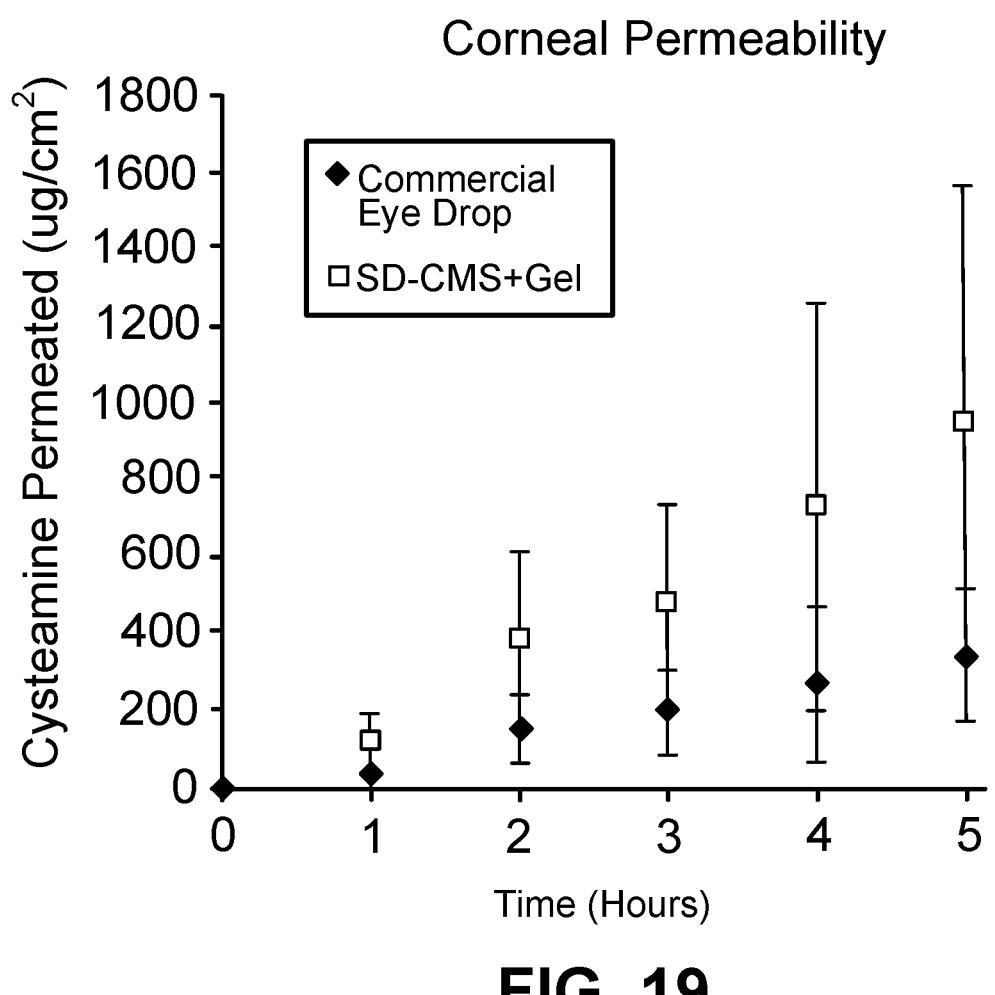
FIG. 19 is a graph showing the corneal permeability of cysteamine released from SD-CMSs suspended in a thermoresponsive gel matrix as compared to a commercial eye drop.

The ability of cysteamine released from SD-CMSs suspended in a thermoresponsive gel matrix to permeate across the cornea was evaluated. Cysteamine released from SD-CMSs suspended in a thermoresponsive gel matrix permeated through an ex vivo cornea in about 5 hours (FIG. 19). The corneal permeability of cysteamine released from SD-CMSs suspended in a thermoresponsive gel matrix was more efficient than corneal permeability of a commercial eye drop (see, e.g., Pescina et al., *Eur J Pharm Biopharm.* 107:171-9 (2016)).

Figure 20A:
FIGS. 20A and 20B show the stability of cysteamine.
Figure 20B:
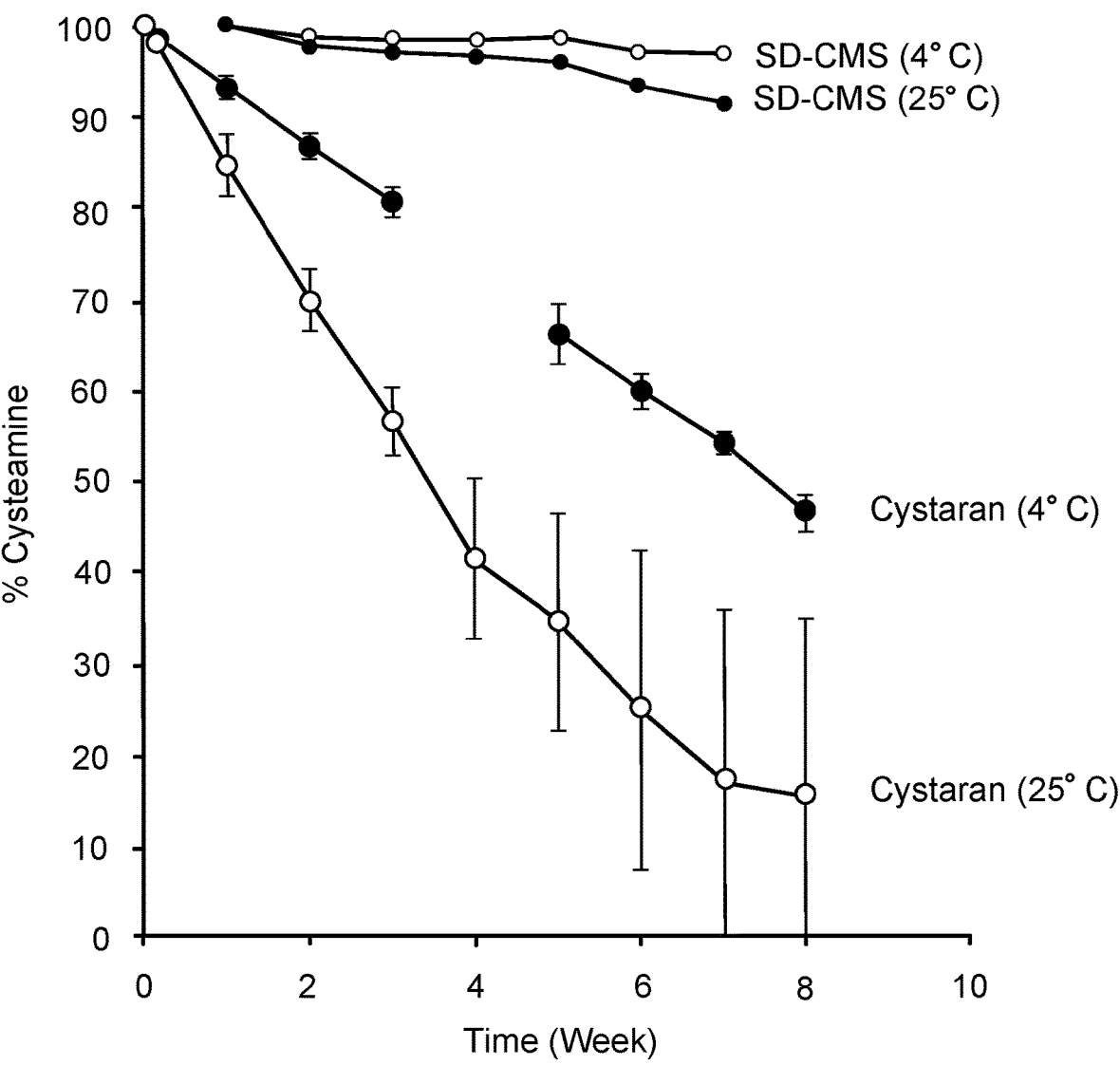

The stability of SD-CMSs suspended in a thermoresponsive gel matrix was evaluated using NMR (FIG. 20A). SD-CMSs suspended in a thermoresponsive gel matrix maintain at least 90% of the cysteamine content for at least 7 weeks (FIG. 20B). Cysteamine released from SD-CMSs suspended in a thermoresponsive gel matrix was more stable than cysteamine in a Cystaran® eye drop (FIG. 20B).

Example 4: Treatment of Cystinosis

A subject diagnosed with cystinosis is selected. The subject may be diagnosed with cystinosis by measuring cystine levels in white blood cells, particularly polymorphonuclear leukocytes or by detection of characteristic symptoms such as cystine crystals within the cornea, which can be detected using a slit lamp. Diagnosis also may be made by genetic testing to identify the characteristic CTNS gene mutation that causes the disorder.

The subject is administered a therapeutically effective dose of the ocular delivery system at periodic intervals. In some embodiments, the ocular delivery system is administered to the lower fornix of each eye. The therapeutically effective dose may be one or two drops of the ocular delivery system, wherein the ocular delivery system has a concentration of 0.001 mg to 0.35 mg cysteamine or a pharmaceutically acceptable salt thereof per microliter of the ocular delivery system. Each drop may have a volume of from 25-75 µL. A dose of the ocular delivery system may be administered once a day, once every two days, once every three days, once every five days, or once every seven days. The administered drop forms a gelled member within the eye as it warms to body temperature (see FIGS. 1A-1C). The gelled member is removed prior to administering a subsequent dose of the ocular delivery system. The gelled member may be removed by flushing the eye with saline or by any other suitable method, such as carefully removing the gelled member with tweezers. In some embodiments, administration of the ocular delivery system to the subject is continued for the subject's lifetime.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An ocular delivery system for cysteamine, comprising:
   a thermoresponsive gel comprising poly(N-isopropyl acrylamide) (PNIPAAm); and
   a plurality of spray-dried microparticles comprising a biodegradable polymer and cysteamine or a pharmaceutically acceptable salt thereof, wherein said biodegradable polymer comprises poly(lactic-co-glycolic acid) (PLGA),
   wherein at least 90 percent of said cysteamine or said pharmaceutically acceptable salt thereof is maintained within said ocular delivery system for at least seven weeks at 25° C.

2. The ocular delivery system of claim 1, wherein the biodegradable polymer comprises polyglycolide (PGA), poly(lactic acid) (PLA), poly(lactic-co-glycolic acid) (PLGA), or any combination thereof.

3. The ocular delivery system of claim 1, wherein the cysteamine or the pharmaceutically acceptable salt thereof is homogeneously dispersed within the spray-dried microparticles.

4. The ocular delivery system of claim 1, wherein the spray-dried microparticles have a volume average diameter within a range of from 200 nm to 10 μm.

5. The ocular delivery system of claim 1, wherein the spray-dried microparticles comprise from 10-20 wt % cysteamine or an amount of a pharmaceutically acceptable salt of cysteamine sufficient to provide 10-20 wt % cysteamine.

6. The ocular delivery system of claim 1, wherein the PLGA has a weight average molecular weight within a range of 4-80 kDa.

7. The ocular delivery system of claim 1, wherein the ocular delivery system comprises from 0.001 mg to 0.5 mg of the spray-dried microparticles per microliter of the ocular delivery system.

8. An ocular delivery system for cysteamine made by a process comprising:
   providing a liquid feedstock comprising cysteamine or a pharmaceutically acceptable salt thereof, a biodegradable polymer, and a solvent, wherein the biodegradable polymer comprises poly(lactic-co-glycolic acid) (PLGA);
   directing the liquid feedstock to a spray-drying apparatus comprising a drying chamber comprising an inlet and an outlet, a nozzle coupled to the inlet, a spray gas source coupled to the nozzle, a separator coupled to the outlet of the drying chamber, and an aspirator coupled to the separator;
   atomizing the liquid feedstock into droplets as the liquid feedstock flows through the nozzle and into the drying chamber;
   removing at least a portion of the solvent from the droplets in the drying chamber, thereby forming a plurality of spray-dried microparticles, wherein the spray-dried microparticles comprise a solid dispersion of the cysteamine, or the pharmaceutically acceptable salt thereof, and the biodegradable polymer;
   collecting the spray-dried microparticles; and
   dispersing the spray-dried microparticles in a thermoresponsive gel comprising poly(N-isopropyl acrylamide) (PNIPAAm) to form an ocular delivery system for cysteamine,
   wherein at least 90 percent of said cysteamine or said pharmaceutically acceptable salt thereof is maintained within said ocular delivery system for at least seven weeks at 25° C.

* * * * *